United States Patent
Takeshima

(10) Patent No.: US 11,734,817 B2
(45) Date of Patent: Aug. 22, 2023

(54) MEDICAL INFORMATION PROCESSING APPARATUS, MAGNETIC RESONANCE IMAGING APPARATUS, AND MEDICAL INFORMATION PROCESSING METHOD

(71) Applicant: CANON MEDICAL SYSTEMS CORPORATION, Otawara (JP)

(72) Inventor: Hidenori Takeshima, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 410 days.

(21) Appl. No.: 16/436,132

(22) Filed: Jun. 10, 2019

(65) Prior Publication Data
US 2019/0378271 A1 Dec. 12, 2019

(30) Foreign Application Priority Data
Jun. 11, 2018 (JP) .................................. 2018-111410

(51) Int. Cl.
| | |
|---|---|
| *G16H 10/60* | (2018.01) |
| *G06Q 10/10* | (2023.01) |
| *G06N 20/00* | (2019.01) |
| *G06T 7/00* | (2017.01) |
| *G16H 30/00* | (2018.01) |
| G16H 50/30 | (2018.01) |

(52) U.S. Cl.
CPC .......... *G06T 7/0012* (2013.01); *G16H 10/60* (2018.01); *G16H 30/00* (2018.01); *G06N 20/00* (2019.01); *G06Q 10/10* (2013.01); *G16H 50/30* (2018.01)

(58) Field of Classification Search
CPC ...... G06T 7/0012; G16H 10/60; G16H 30/00; G16H 50/30; G06N 20/00; G06Q 10/10
See application file for complete search history.

(56) References Cited

U.S. PATENT DOCUMENTS

| | | | | |
|---|---|---|---|---|
| 10,510,000 B1 * | 12/2019 | Commons | .............. | G06N 3/045 |
| 2015/0190106 A1 | 7/2015 | Yamakawa et al. | | |
| 2017/0007187 A1 * | 1/2017 | Breneisen | .............. | G16H 40/63 |
| 2017/0337713 A1 * | 11/2017 | Hoelzer | ................ | G06T 11/003 |
| 2019/0059780 A1 * | 2/2019 | Lee | ....................... | A61B 5/7264 |

FOREIGN PATENT DOCUMENTS

| | | |
|---|---|---|
| JP | 2006-25868 A | 2/2006 |
| JP | 2017-225688 | 12/2017 |
| WO | WO 2014/041889 A1 | 3/2014 |

OTHER PUBLICATIONS

Chen Wang, et al., "Kervolutional Neural Networks", arXiv:1904.03955v1[cs.CV], 2019, 10 pages.
Japanese Office Action dated Aug. 23, 2022 in Japanese Patent Application No. 2018-111410, 3 pages.

* cited by examiner

*Primary Examiner* — Jay M. Patel
(74) *Attorney, Agent, or Firm* — Oblon, McClelland, Maier & Neustadt, L.L.P.

(57) ABSTRACT

According to one embodiment, a medical information processing apparatus includes at least one processor. The processor is configured to execute a program to acquire first data collected from a test object, input the acquired first data into a first model, determine whether second data, which is output from the first model receiving the first data, is to be input into a second model, and in a case where the processor determines that the second data is to be input into the second model, input the second data into the second model, and output third data which is output from the second model receiving the second data.

16 Claims, 10 Drawing Sheets

FIG. 11

| ORDER | DETAILS | EXECUTION TIME | EVALUATION CONDITIONS |
|---|---|---|---|
| 1 | PHOTOGRAPHING WITHOUT CONTRAST MEDIUM ADMINISTRATION | T1 (LONG) | LOOSE |
| 2 | PHOTOGRAPHING WITHOUT CONTRAST MEDIUM ADMINISTRATION | T2 (LONG) | LOOSE |
| 3 | PHOTOGRAPHING WITH CONTRAST MEDIUM ADMINISTRATION | T3 (SHORT) | STRICT |
| 4 | PHOTOGRAPHING WITHOUT CONTRAST MEDIUM ADMINISTRATION | T4 (LONG) | LOOSE |
| ... | ... | ... | ... |

MEDICAL INFORMATION PROCESSING APPARATUS, MAGNETIC RESONANCE IMAGING APPARATUS, AND MEDICAL INFORMATION PROCESSING METHOD

CROSS-REFERENCE TO RELATED APPLICATION

The present application claims priority based on Japanese Patent Application No. 2018-111410, filed on Jun. 11, 2018, the content of which is incorporated herein by reference.

FIELD

Embodiments described herein relate generally to a medical information processing apparatus, a magnetic resonance imaging apparatus, and a medical information processing method.

BACKGROUND

In the related art, there is a known technique for reconstructing an image using an echo signal, performing various analyses and computations on a generated diffusion weighted image and displaying a generated image, GUI and the like on a display. Such technique further includes generating a learning model for performing image pattern recognition using a machine learning algorithm, learning a technique most suitable for correcting an image using pixels, various reference values, and correction values for each portion of a body using a machine learning algorithm, and generating a model for determining an optimal correction method from pixels.

When medical images are generated using machine learning in the related art, there are cases where generating medical images with high accuracy and decreasing a processing time have a trade-off relationship and thus it is difficult to improve both with balance.

BRIEF DESCRIPTION OF THE DRAWINGS

FIG. 11 is a diagram showing an example of a photographing schedule.

DETAILED DESCRIPTION

According to one embodiment, a medical information processing apparatus includes at least one processor. The processor is configured to execute a program to acquire first data collected from a test object, input the acquired first data into a first model, determine whether second data, which is output from the first model receiving the first data, is to be input into a second model, and in a case where the processor determines that the second data is to be input into the second model, input the second data into the second model, and output third data which is output from the second model receiving the second data. A medical information processing apparatus of an embodiment is to generate medical images with high accuracy while decreasing a processing time.

Hereinafter, embodiments of a medical information processing apparatus, a magnetic resonance imaging apparatus, and a medical information processing method will be described in detail with reference to the drawings.

First Embodiment

Figure 1:
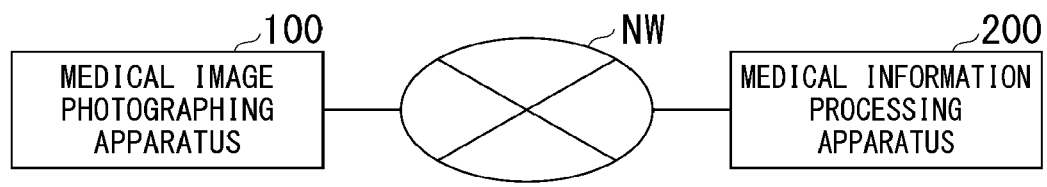
FIG. 1 is a diagram showing an example of a configuration of a medical information processing system including a medical information processing apparatus according to a first embodiment.

FIG. 1 is a diagram showing an example of a configuration of a medical information processing system 1 including a medical information processing apparatus 200 according to a first embodiment. For example, the medical information processing system 1 includes a medical image photographing apparatus 100 and the medical information processing apparatus 200, as shown in FIG. 1. The medical image photographing apparatus 100 and the medical information processing apparatus 200 are connected through a network NW. Examples of the network NW include a wide area network (WAN), a local area network (LAN), the Internet, a dedicated line, a wireless base station, a provider, and the like.

Examples of the medical image photographing apparatus 100 include a magnetic resonance imaging (MRI) apparatus, a computed tomography (CT) apparatus, and the like. For example, an MRI apparatus is an apparatus that generates a medical image (MR image) by applying magnetic fields to a test object (e.g., a human body), receiving electromagnetic waves generated from hydrogen nuclei in the test object according to nuclear magnetic resonance using a coil and reconstructing a signal based on the received electromagnetic waves. For example, the CT apparatus is an apparatus that generates a medical image (CT image) by radiating X rays to a test object from an X-ray tube rotating around the test object, detecting X rays that have passed through the test object and reconstructing a signal based on the detected X rays. In the following description, the medical image photographing apparatus 100 is described as an MRI apparatus as an example.

The medical information processing apparatus 200 is implemented as one or a plurality of processors. For example, the medical information processing apparatus 200 may be a computer included in a cloud computing system or a computer (stand-alone computer) operating alone without depending on other apparatuses.

[Example of Configuration of Medical Image Photographing Apparatus]

Figure 2:
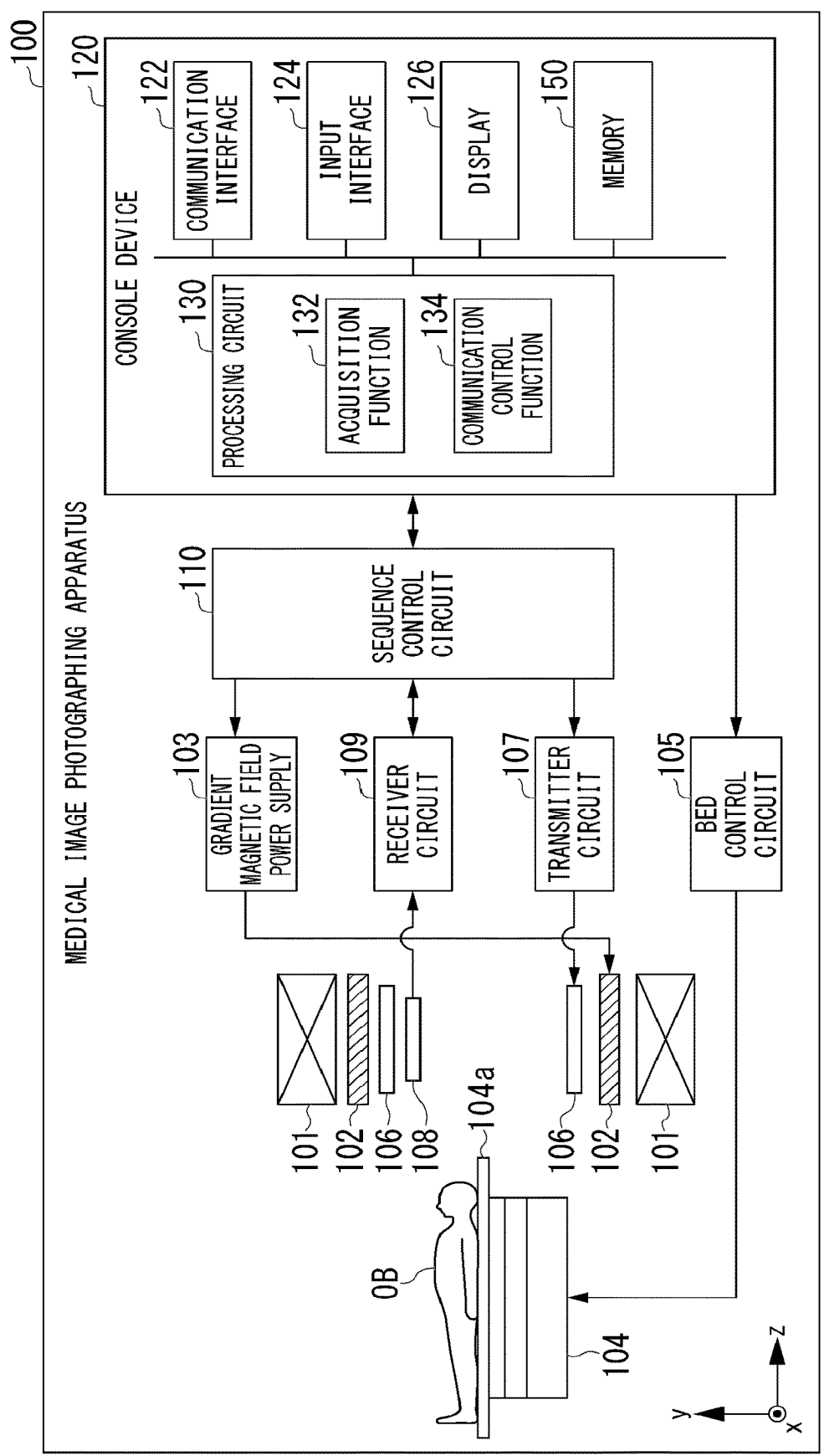
FIG. 2 is a diagram showing an example of a medical image photographing apparatus according to the first embodiment.

FIG. 2 is a diagram showing an example of the medical image photographing apparatus 100 according to the first embodiment. As shown in FIG. 2, the medical image photographing apparatus 100 includes a static magnetic field magnet 101, a gradient magnetic field coil 102, a gradient magnetic field power supply 103, a bed 104, a bed control circuit 105, a transmission coil 106, a transmitter circuit 107, a reception coil 108, a receiver circuit 109, a sequence control circuit 110, and a console device 120.

The static magnetic field magnet 101 is a magnet formed in a hollow approximately cylindrical shape and generates a uniform static magnetic field in the inner space. For example, the static magnetic field magnet 101 is a permanent magnet, a superconducting magnet or the like. The gradient magnetic field coil 102 is a coil formed in a hollow approximately cylindrical shape and is provided inside the static magnetic field magnet 101. The gradient magnetic field coil 102 is a combination of three coils corresponding to x, y and z axes orthogonal to one another. The z-axis direction represents a longitudinal direction of a top plate 104a of the bed 104, the x-axis direction represents an axial direction perpendicular to the z-axis direction and parallel with the floor of a room in which the medical image photographing apparatus 100 is installed, and the y-axis direction represents an axial direction perpendicular to the floor. The three coils corresponding to the axial directions are individually provided with a current from the gradient magnetic field power supply 103 and generate gradient magnetic fields whose magnetic field intensity changes along the respective x, y and z axes. Meanwhile, the z-axis direction is the same direction as static magnetic fields.

The gradient magnetic field power supply 103 supplies a current to the gradient magnetic field coil 102. Gradient magnetic fields of the x, y and z axes generated by the gradient magnetic field coil 102 respectively correspond to, for example, a slice selection gradient magnetic field Gs, a phase encoding gradient magnetic field Ge, and a readout gradient magnetic field Gr. The slice selection gradient magnetic field Gs is used to determine an imaging slice at will. The phase encoding gradient magnetic field Ge is used to change the phase of a magnetic resonance signal in accordance with the spatial position. The readout gradient magnetic field Gr is used to change the frequency of a magnetic resonance signal in accordance with the spatial position.

The bed 104 includes a top plate 104a on which a test object OB is placed, and the top plate 104a is inserted into a hollow space (image capture opening) of the gradient magnetic field coil 102 under the control of the bed control circuit 105 while the test object OB is placed thereon. In general, the bed 104 is installed in such a manner that the longitudinal direction thereof extends parallel to the central axis of the static magnetic field magnet 101. The bed control circuit 105 drives the bed 104 to move the top plate 104a in the longitudinal direction and vertical direction under the control of the console device 120.

The transmission coil 106 is provided inside the gradient magnetic field coil 102. The transmission coil 106 receives a supply of a radio frequency (RF) pulse from the transmitter circuit 107 and generates a radio frequency magnetic field. The transmitter circuit 107 supplies the transmission coil 106 with the RF pulse corresponding to a Larmor frequency determined by the type of a targeted atom and intensities of magnetic fields.

The reception coil 108 is provided inside the gradient magnetic field coil 102. The reception coil 108 receives magnetic resonance signals emitted from the test object OB due to an influence of the radio frequency magnetic field. When the reception coil 108 has received the magnetic resonance signals, the reception coil 108 outputs the received magnetic resonance signals to the receiver circuit 109. Meanwhile, the reception coil 108 is a coil array having one or more, typically a plurality of, reception coils in the first embodiment. Hereinafter, when the reception coil is a coil array, each coil constituting the array will be referred to as a coil element.

The receiver circuit 109 generates magnetic resonance data based on the magnetic resonance signals output from the reception coil 108. Specifically, the receiver circuit 109 generates the magnetic resonance data that is a digital signal by performing analog-to-digital conversion on the magnetic resonance signals output from the reception coil 108. In addition, the receiver circuit 109 transmits the generated magnetic resonance data to the sequence control circuit 110. Meanwhile, the receiver circuit 109 may be provided on the side of a gantry device including the static magnetic field magnet 101, the gradient magnetic field coil 102 and the like. Magnetic resonance signals output from the respective coil elements of the reception coil 108 are appropriately distributed and combined and output to the receiver circuit 109.

The sequence control circuit 110 photographs the test object OB by driving the gradient magnetic field power supply 103, the transmitter circuit 107 and the receiver circuit 109 based on sequence information transmitted from the console device 120. The sequence information is information defining a procedure for performing an imaging process. The sequence information includes information defining the intensity of power supplied from the gradient magnetic field power supply 103 to the gradient magnetic field coil 102, a timing at which the power is supplied, the intensity of an RF pulse transmitted from the transmitter circuit 107 to the transmission coil 106, a timing at which the RF pulse is applied, a timing at which the receiver circuit 109 detects magnetic resonance signals, and the like.

Further, the sequence control circuit 110 images the test object OB by driving the gradient magnetic field power supply 103, the transmitter circuit 107 and the receiver circuit 109, and when magnetic resonance data has been received from the receiver circuit 109, transfers the received magnetic resonance data to the console device 120.

The console device 120 performs overall control of the medical image photographing apparatus 100 or collects magnetic resonance data. For example, the console device 120 includes a communication interface 122, an input interface 124, a display 126, a processing circuit 130, and a memory (storage) 150.

For example, the communication interface 122 includes a communication interface such as a network interface card (NIC). The communication interface 122 communicates with the medical information processing apparatus 200 through the network NW and receives information from the medical information processing apparatus 200. The communication interface 122 outputs the received information to the processing circuit 130. Further, the communication interface 122 may transmit information to other devices connected through the network NW under the control of the processing circuit 130.

The input interface 124 receives various input operations from an operator, converts the received input operations into electrical signals and outputs the electrical signals to the processing circuit 130. For example, the input interface 124 is implemented as a mouse, a keyboard, a track ball, a switch, a button, a joystick, a touch panel or the like. In addition, the input interface 124 may be implemented as a user interface that receives voice input, such as a microphone, for example. When the input interface 124 is a touch panel, the display 126 which will be described later may be integrated with the input interface 124.

The display 126 displays various types of information. For example, the display 126 displays images generated by the processing circuit 130, a graphical user interface (GUI) for receiving various input operations from an operator, and the like. For example, the display 126 is a liquid crystal display (LCD), a cathode ray tube (CRT) display, an organic electroluminescence (EL) display, or the like.

The processing circuit 130 executes an acquisition function 132 and a communication control function 134, for example. The processing circuit 130 realizes these functions, for example, by causing a hardware processor provided in the computer to execute a program stored in the memory 150, which is a storage device (storage circuit).

The hardware processor for realizing each function of the processing circuit 130 means, for example, a circuit (circuitry) such as a central processing unit (CPU), a graphics processing unit (GPU), an application specific integrated circuit (ASIC), or a programmable logic device (PLD). Examples of PLDs include a simple programmable logic device (SPLD), a complex programmable logic device (CPLD), a field programmable gate array (FPGA), or the like. Instead of storing the program in the memory 150, the program may be directly incorporated in the circuit of the hardware processor. In this case, the hardware processor realizes the above functions by reading and executing a program embedded in the circuit. The hardware processor is not limited to being configured as a single circuit, and a plurality of independent circuits may be combined to be configured as one hardware processor to realize each function. Also, multiple components may be integrated into one hardware processor to realize each function.

The memory 150 is implemented as a semiconductor memory element such as a random-access memory (RAM) or a flash memory, a hard disk, an optical disc, or the like. These non-transitory storage media may be implemented as other storage devices connected through the network NW, such as a network attached storage (NAS) and an external storage device. Further, the non-transitory storage constituting the memory 150 may include a storage medium such as a read only memory (ROM) or a register.

The acquisition function 132 acquires magnetic resonance data from the sequence control circuit 110. The magnetic resonance data is data acquired by performing analog-to-digital conversion on an electromagnetic wave signal (nuclear magnetic resonance signal) generated in the test object OB according to nuclear magnetic resonance, as described above. In the following description, the magnetic resonance data is referred to as "k-space data Dk." A k space represents a space (a space in which the k-space data Dk is arranged) in which one-dimensional waveforms are collected when nuclear magnetic resonance signals are repeatedly collected by the reception coil 108 as the one-dimensional waveforms. The k-space data Dk is an example of "first data."

Figure 3:
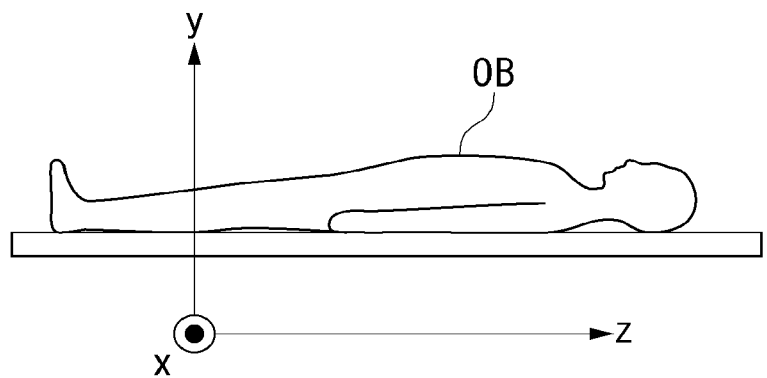
FIG. 3 is a diagram showing k-space data.
Figure 4:
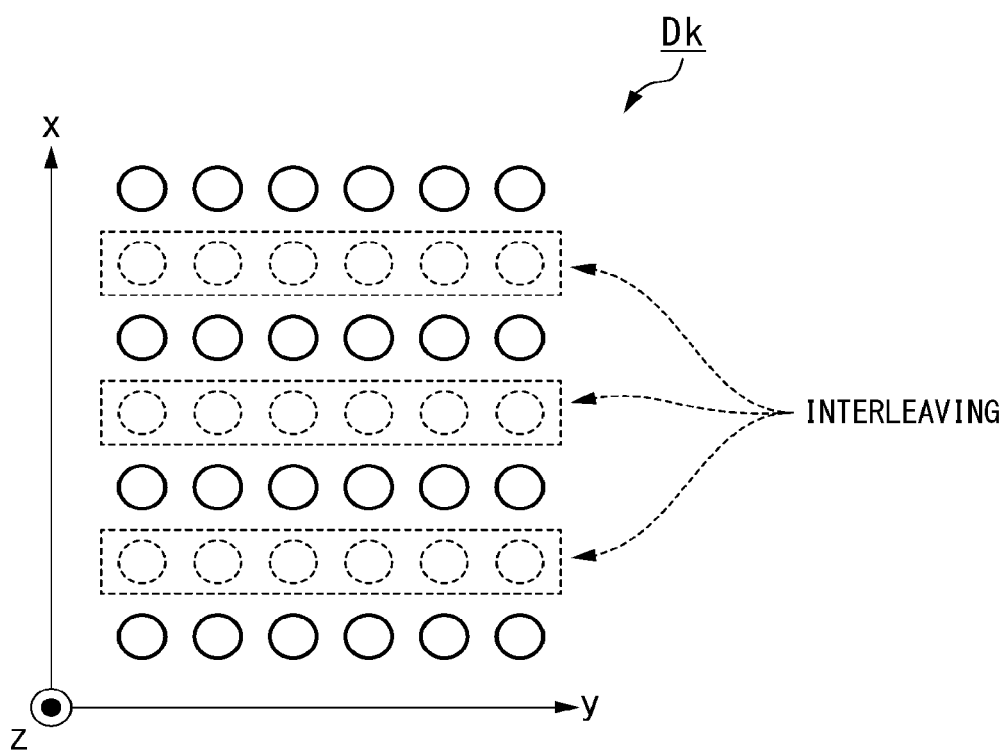
FIG. 4 is a diagram showing the k-space data.

FIG. 3 and FIG. 4 are diagrams showing the k-space data Dk. As shown in FIG. 3, when a real space in which the test object OB is present is represented by x-y-z coordinates, there is a case where the medical image photographing apparatus 100 images the test object OR at a higher speed by interleaving and collecting the k-space data Dk with respect to a certain axial direction (the x direction in the shown example) using a half-Fourier method, for example. In such a case, the k-space data Dk becomes sparse (interleaved) data in the k space as shown in FIG. 4. Although the k-space data Dk is interleaved and collected by the medical image photographing apparatus 100 in the following description as an example, the k-space data Dk need not particularly be interleaved.

When the k-space data Dk has been acquired through the acquisition function 132, the communication control function 134 causes the communication interface 202 to communicate with the medical information processing apparatus 200 to transmit the k-space data Dk to the medical information processing apparatus 200 which is the communication partner. In addition, the communication control function 134 causes the communication interface 202 to communicate with the medical information processing apparatus 200 to acquire a reconstructed image from the medical information processing apparatus 200 which is the communication partner. When the reconstructed image is acquired, the communication control function 134 may output the reconstructed image to the display 126. Accordingly, the reconstructed image is displayed on the display 126.

[Example of Configuration of Medical Information Processing Apparatus]

Figure 5:
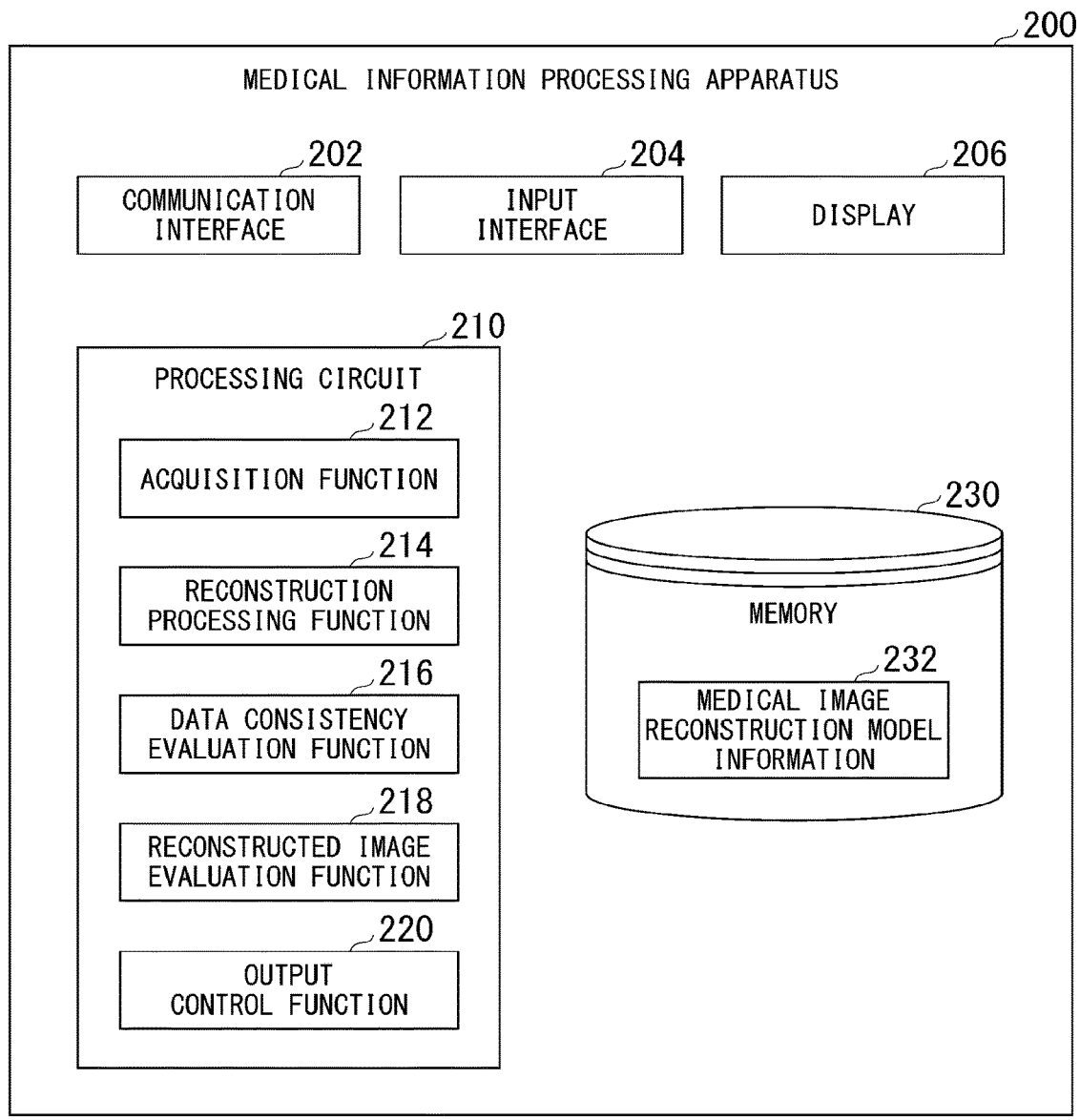
FIG. 5 is a diagram showing an example of the medical information processing apparatus according to the first embodiment.

FIG. 5 is a diagram showing an example of the medical information processing apparatus 200 according to the first embodiment. As shown in FIG. 5, the medical information processing apparatus 200 includes a communication interface 202, an input interface 204, a display 206, a processing circuit 210 and a memory 230, for example.

The communication interface 202 includes a communication interface such as an NIC, for example. The communication interface 202 communicates with the medical image photographing apparatus 100 through the network NW and receives information from the medical image photographing apparatus 100. The communication interface 202 outputs the received information to the processing circuit 210. Further, the communication interface 202 may transmit information to other devices connected through the network NW under the control of the processing circuit 210. The other devices may be terminal devices which can be used by diagnostic image readers such as doctors and nurses, for example.

The input interface 204 receives various input operations from an operator, converts the received input operations into electrical signals and outputs the electrical signals to the processing circuit 210. For example, the input interface 204 is implemented as a mouse, a keyboard, a track ball, a switch, a button, a joystick, a touch panel, or the like. In addition, the input interface 204 may be implemented as a user interface that receives voice input, such as a microphone, for example. When the input interface 204 is a touch panel, the display 206 which will be described later may be integrated with the input interface 204.

The display 206 displays various types of information. For example, the display 206 displays images (reconstructed images which will be described later) generated by the processing circuit 210, a graphical user interface (GUI) for receiving various input operations from an operator, and the like. For example, the display 206 is an LCD, a CRT display, an organic EL display, or the like.

The processing circuit 210 executes an acquisition function 212, a reconstruction processing function 214, a data consistency evaluation function 216, a reconstructed image evaluation function 218, and an output control function 220, for example.

The processing circuit 210 realizes these functions, for example, by causing a hardware processor provided in the computer to execute a program stored in the memory 230, which is a storage device (storage circuit). The hardware processor for realizing each function of the processing circuit 210 means, for example, a circuit (circuitry) such as a CPU, a GPU, an ASIC, or a PLD. Instead of storing the program in the memory 230, the program may be directly incorporated in the circuit of the hardware processor. In this case, the hardware processor realizes the above functions by reading and executing a program embedded in the circuit. The hardware processor is not limited to being configured as a single circuit, and a plurality of independent circuits may be combined to be configured as one hardware processor to realize each function. Also, multiple components may be integrated into one hardware processor to realize each function.

The memory 230 is implemented as a semiconductor memory element such as a RAM or a flash memory, a hard disk, an optical disc, or the like. These non-transitory storage media may be implemented as other storage devices connected through the network NW, such as a NAS and an external storage device. Further, the memory 230 may include a non-transitory storage medium such as a ROM or a register. For example, medical image reconstruction model information 232 and the like are stored in the memory 230. This will be described later.

The acquisition function 212 causes the communication interface 202 to communicate with the medical image photographing apparatus 100 to acquire the k-space data Dk from the medical image photographing apparatus 100 which is the communication partner.

The reconstruction processing function 214 reconstructs a medical image (MR image) from the k-space data Dk acquired through the acquisition function 212 according to a medical image reconstruction model 300 represented by the medical image reconstruction model information 232. For example, the k-space data Dk may be represented by a matrix having rows in one of the x-axis direction and the y-axis direction and columns in the other axial direction. In this case, each element of the matrix representing the k-space data Dk is represented as a multidimensional vector. When the k-space data Dk is interleaved, as described above, element values corresponding to the interleaved k-space data Dk are associated with, for example, predetermined values (e.g., 0) recognizable as element values corresponding to the k-space data Dk which has not been interleaved or predetermined data representation (e.g., null) in the matrix representing the k-space data Dk.

The medical image reconstruction model information 232 is information (a program or a data structure) defining the medical image reconstruction model 300. For example, the function of the medical image reconstruction model 300 may be implemented as a part of the reconstruction processing function 214 by a processor executing the medical image reconstruction model information 232. The medical image reconstruction model 300 includes a plurality of deep neural networks (DNNs) connected in series, for example.

For example, the medical image reconstruction module information 232 includes combination information representing how units included in an input layer, one or more hidden layers (middle layers) and an output layer constituting each DNN are combined, weight information representing the number of coupling coefficients assigned to data input and output between linked units, and the like. For example, the combination information includes information such as the number of units included in each layer, information designating the type of a units that is a combination destination of each units, an activation function that implemented each units, and gates provided between units of the hidden layers. The activation function that realizes a units may be a normalized linear function (ReLU function) or another function such as a Sigmoid function, a step function, or a hyperbolic tangent function, for example. A gate selectively passes or weights data transferred between units in response to a value (e.g., 1 or 0) returned according to the activation function, for example. The coupling coefficient is a parameter of the activation function and includes a weight assigned to output data when the data is output from a certain layer to a deeper layer in a hidden layer of a neural network, for example. Further, the coupling coefficient may include a unique bias component of each layer, and the like.

[Example of Configuration of Medical Image Reconstruction Model]

Figure 6:
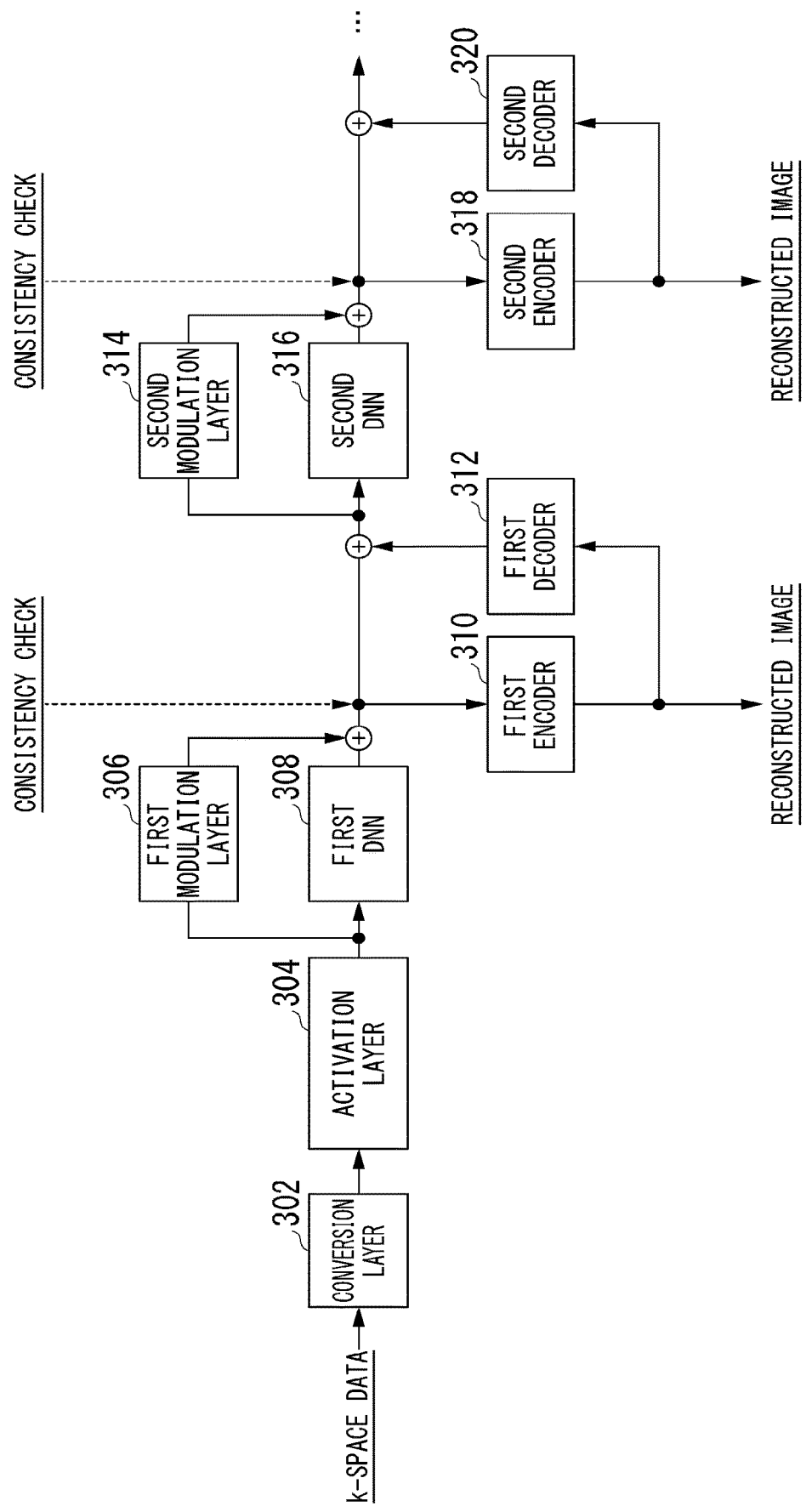
FIG. 6 is a diagram showing an example of a medical image reconstruction model.

FIG. 6 is a diagram showing an example of the medical image reconstruction model 300. In the shown example, the medical image reconstruction model 300 represents a model in which two DNNs are connected in series. As shown, the medical image reconstruction model 300 may include a conversion layer 302, an activation layer 304, a first modulation layer 306, a first DNN 308, a first encoder 310, a first decoder 312, a second modulation layer 314, a second DNN 316, a second encoder 318, and a second decoder 320, for example. Meanwhile, although the medical image reconstruction model 300 has two DNNs in the shown example, the present embodiment is not limited thereto and three or more DNNs may be provided.

DNN can be represented by a plurality of linear functions including parameters such as weighting factors and bias components, and a plurality of activation functions. In other words, the medical image reconstruction model 300 can be understood as a composite function (a composite function with parameters) acquired by combining a plurality of linear functions whose parameters can be determined by learning and a plurality of non-linear functions whose parameters cannot be determined by learning.

A combination of the first DNN 308, the first encoder 310 and the first decoder 312 is an example of a "first model." The second DNN 316, the second encoder 318 and the second decoder 320 are an example of a "second model." Meanwhile, when the medical image reconstruction model 300 is composed of DNNs of three stages or more, any one of the three or more DNNs included in the medical image reconstruction model 300 may be a part of the "first model" and a DNN provided after the DNN corresponding to the "first model" may be a part of the "second model."

For example, a matrix representing k-space data Dk is input to the conversion layer 302. The conversion layer 302 may be a hidden layer called a convolutional layer included in a convolutional neural network (CNN) or the like, for example. The convolutional layer convolutes a predetermined filter (multiplies a window function) for an input matrix and compresses each element of the matrix overlapping with the filter into one unit matrix. Such a hidden layer is also called an encoder. A unit matrix may be represented by a matrix having an arbitrary dimensionality, for example. In a unit matrix, a single variable value (feature value) acquired through convolution is associated as an element value of the matrix.

For example, the conversion layer 302 repeats convolution processing while shifting a filter on the k-space data Dk that is a matrix to generate a plurality of unit matrices. For example, the conversion layer 302 repeats convolution processing 128 times to generate 128 unit matrices. In the following description, there is a case where each unit matrix is represented as a channel. The conversion layer 302 outputs the generated plurality of unit matrices to the activation layer 304.

The activation layer 304 may be implemented as a pooling layer, an activation function such as the aforementioned ReLU or Sigmoid function, or the like, for example. When the activation layer 304 is a pooling layer, the activation layer 304 compresses the dimensionality of unit matrices by exchanging element values of the unit matrices with representative values such as average values or maximum values of all element values included in the unit matrices. In addition, when the activation function of each node included in the activation layer 304 is a ReLU, a Sigmoid function, or the like, the activation layer 304 sets each element value of unit matrices output by the conversion layer 302 to zero when the element value is a negative value, and decreases the element value as the element value becomes close to 0 and increases the element value as the element value becomes far from 0 when the element value is a positive value. Then, the activation layer 304 outputs the processed unit matrices to the first modulation layer 306 and the first DNN 308.

The first modulation layer 306 may be implemented as a layer of multiplying a weight, a layer of performing scaling, or the like, for example. When the first modulation layer 306 is a layer of multiplying a weight, for example, an activation function of each node of the first modulation layer 306 may be a step function of setting a weight to be multiplied by an element value of a unit matrix to 1 when the element value is equal to or less than a threshold value and setting the weight to be multiplied by the element value to 0 when the element value exceeds the threshold value. That is, the first modulation layer 306 may be a low pass filter for diminishing an element value higher than the threshold value.

The first DNN 308 may be implemented as any one of various neural networks such as the aforementioned CNN, recurrent neural network (RNN), and fully-connected neural network (FCNN) or a combination of a plurality of neural networks, for example. In the present embodiment, the type of the first DNN 308 is not particularly limited and the first DNN 308 may be implemented as any neural network.

For example, the first DNN 308 predicts feature values which are sources of k-space data Dk (element values) that is not present due to interleaving on the assumption that the k-space data Dk acquired through the acquisition function 212 is interleaved data of the k-space data Dk, and is learned to output a matrix having the predicted feature values as element values. That is, the first DNN 308 is learned to output unit matrices which become the source of k-space data Dk which complements data that is not present due to interleaving. Accordingly, when a plurality of unit matrices is input from the activation layer 304, the first DNN 308 predicts feature values which may be acquired from k-space data Dk that should be originally collected with respect to unit matrices for which feature values acquired through convolution with a filter decrease because the original k-space data Dk is not present, for example. As a result, the first DNN 308 generates one (one channel) unit matrix having the predicted feature values as element values from the input plurality of unit matrices (e.g., unit matrices of 128 channels).

For example, the first encoder 310 is implemented as a convolution layer. For example, the first encoder 310 generates a matrix having the same numbers of rows and columns as the k-space data Dk based on output data from the first modulation layer 306 and output data from the first DNN 308. When 128 unit matrices (128 channels) are input to the first DNN 308, for example, 128 unit matrices are also input to the first modulation layer 306. Accordingly, 128 unit matrices are output from the first modulation layer 306. The first encoder 310 generates one (one channel) matrix based on a total of 129 unit matrices (129 channels) acquired by concatenating one unit matrix output from the first DNN 308 to 128 unit matrices output from the first modulation layer 306. This matrix is a matrix having the k-space data Dk predicted by the first DNN 308 as element values and having the same numbers of rows and columns as the matrix of the k-space data Dk.

The first encoder 310 generates a medical image (hereinafter referred to as a reconstructed image) reconstructed using the k-space data Dk by performing an inverse Fourier transform on the generated matrix and outputs the medical image. Further, the first encoder 310 may output the generated matrix as it is without performing an inverse Fourier transform or while performing an inverse Fourier transform. The reconstructed image or matrix output from the first encoder 310 is an example of "second data."

The first decoder 312 is implemented as, for example, a convolution layer. When the reconstructed image has been output from the first encoder 310, for example, the first decoder 312 generates a matrix having each of a plurality of pieces of k-space data Dk as an element value from the reconstructed image by performing a Fourier transform on the reconstructed image. In addition, when the first encoder 310 has output a matrix having the k-space data Dk as element values instead of the reconstructed image, the first decoder 312 may not perform a Fourier transform. The matrix output from the first decoder 312 is another example of the "second data."

The first decoder 312 generates a plurality of unit matrices by repeating convolution processing while shifting a filter on the matrix generated by performing a Fourier transform on the reconstructed image output from the first encoder 310 or the matrix output from the first encoder 310. For example, the first decoder 312 may generate 128 unit matrices (128 channels) by repeating convolution processing 128 times like the conversion layer 302. The first decoder 312 outputs the generated plurality of unit matrices to the second modulation layer 314 and the second DNN 316.

The second modulation layer 314 may be implemented as a layer of multiplying a weight, a layer of performing scaling or the like, for example, like the first modulation layer 306. When the second modulation layer 314 includes a low pass filter, for example, element values may be diminished by exchanging element values greater than a threshold value, among element values of a unit matrix output from the first modulation layer 306, a unit matrix output from the first DNN 308 and a unit matrix output from the first decoder 312, with 0 or the like.

The second DNN 316 may be implemented as any one of various neural networks such as the CNN, RNN and FCNN or a combination of a plurality of neural networks, for example, like the first DNN 308. In the present embodiment, the type of the second DNN 316 is not particularly limited and the second DNN 316 may be implemented as any neural network.

When a certain matrix is input to the second DNN 316, the second DNN 316 is learned to output a different matrix. More specifically, the second DNN 316 is learned to output a unit matrix having feature values, which are sources of k-space data Dk predicted with higher accuracy than the k-space data Dk predicted by the first DNN 308 at the previous stage, as element values when a certain unit matrix is input. Accordingly, when a unit matrix output from the first modulation layer 306, a unit matrix output from the first DNN 308 and a unit matrix output from the first decoder 312 have been input, the second DNN 316 generates one unit matrix having predicted feature values as element values from the plurality of unit matrices.

The second encoder 318 is implemented as a convolution layer, for example. The second encoder 318 generates a matrix having the same numbers of rows and columns as those of the matrix of the k-space data Dk based on output data from the second modulation layer 314 and output data from the second DNN 316, for example. The second encoder 318 generates a reconstructed image which has been reconstructed using the k-space data Dk by performing an inverse Fourier transform on the generated matrix and outputs the reconstructed image. Further, the second encoder 318 may output the generated matrix as it is without performing an inverse Fourier transform or while performing an inverse Fourier transform.

The second decoder 320 is implemented as a convolution layer, for example. When the reconstructed image has been output from the second encoder 318, for example, the second decoder 320 generates a matrix having each of a plurality of pieces of k-space data Dk as an element value from the reconstructed image by performing a Fourier transform on the reconstructed image. In addition, when the second encoder 318 has output a matrix having the k-space data Dk as element values instead of the reconstructed image, the second decoder 320 may not perform a Fourier transform. The reconstructed image or matrix output from the second decoder 320 is an example of "third data."

The second decoder 320 generates a plurality of unit matrices by repeating convolution processing while shifting a filter on the matrix generated by performing a Fourier transform on the reconstructed image output from the second encoder 318 or the matrix directly output from the second encoder 318. For example, the second decoder 320 may generate 128 unit matrices (128 channels) by repeating convolution processing 128 times like the conversion layer 302. The second decoder 320 outputs the generated plurality of unit matrices to a DNN (not shown) at the further subsequent stage. The matrix output from the second decoder 320 is another example of the "third data."

In this manner, the medical image reconstruction model 300 including a plurality of DNNs performing the same type of processing for improving image quality can predict interleaved k-space data Dk with higher accuracy by repeating propagation of a processing result of a DNN provided at a previous stage to a DNN provided at a subsequent stage. In other words, it is possible to generate a reconstructed image with higher accuracy (higher picture quality) when a processing result of a DNN at a previous stage is propagated to a DNN at a further subsequent stage.

Referring back to FIG. 5, the data consistency evaluation function 216 evaluates a matrix before converting into a reconstructed image generated by each encoder included in the medical image reconstruction model 300, that is, the k-space data Dk. For example, the data consistency evaluation function 216 evaluates the k-space data Dk based on mathematical expression (1). Meanwhile, although Cartesian sampling will be described as an example below, the present embodiment can also be applied to non-Cartesian sampling represented by Radial scan by exchanging a matrix MF which will be described below with a Radial scan collection matrix.

[Expression. 1]

$$\vec{y} = M \cdot F \cdot \vec{x} \quad (1)$$

In the expression, $\vec{y}$ denotes a vector that represents each element of k-space data Dk collected by the medical image photographing apparatus 100. $\vec{x}$ denotes a vector that represents each row component of a matrix (matrix before converting into a reconstructed image) generated by each encoder (the first encoder 310, the second encoder 318, or the like). In other words, $\vec{x}$ denotes a vector that represents an element of each piece of k-space data Dk predicted by the medical image reconstruction model 300. ($\rightarrow$) in parentheses represents a vector symbol in the expression.

F and M represent square matrices. The square matrix F represents a matrix of performing a Fourier transform on $\vec{x}$. The square matrix M represents a matrix of masking the element of $\vec{x}$.

Figure 7:
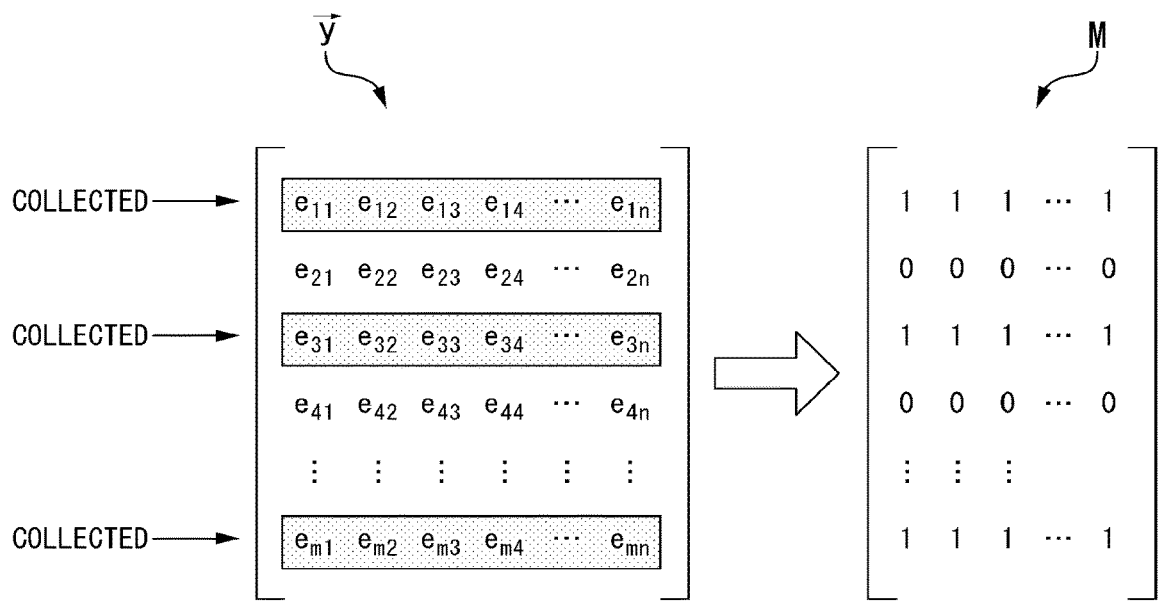
FIG. 7 is a diagram showing an example of a square matrix M.

FIG. 7 is a diagram showing an example of the square matrix M. In the figure, $e_{11}, e_{12}, \ldots, e_{mn}$ denote elements of a matrix representing k-space data Dk collected by the medical image photographing apparatus 100, that is, elements of the k-space data Dk. For example, when k-space data Dk such as the second row and the fourth row are interleaved and collected by the medical image photographing apparatus 100, element values such as $\{e_{21}, e_{22}, \ldots e_{2n}\}$, $\{e_{41}, e_{42}, \ldots, e_{4n}\}$ and the like are exchanged with a predetermined value such as 0 or exchanged with a predetermined data representation such as null. In this case, in the square matrix M, element values of rows in which k-space data Dk has been collected without being interleaved are exchanged with 1 and element values of rows in which k-space data Dk has been interleaved are exchanged with 0. In the shown example, the square matrix M becomes a matrix in which element values of odd-numbered rows are 1 and elements values of even-numbered rows are 0 because odd-numbered rows represent rows in which k-space data Dk has been collected without being interleaved and even-numbered rows represent rows in which k-space data Dk has been interleaved in the matrix representing the k-space data Dk.

In this manner, the left-side term of mathematical expression (1) represents a plurality of pieces of k-space data Dk actually collected by the medical image photographing apparatus 100 and the right-side term of the mathematical expression (1) represents a plurality of pieces of k-space data Dk predicted by the medical image reconstruction model 300. Accordingly, the data consistency evaluation function 216 evaluates consistency between the collected k-space data Dk and the predicted k-space data Dk by comparing the left-side term and the right-side term of mathematical expression (1) with each other and deriving a difference therebetween.

For example, the data consistency evaluation function 216 compares each row vector $\vec{y}$ of a matrix representing acquired k-space data Dk with each row vector $\vec{x}$ of a matrix representing predicted k-space data Dk in units of row to derive a difference between element values for each row.

For example, it is assumed that $\vec{y}$ that is an actually measured value is represented by mathematical expression (2), $\vec{x}$ that is a predicted value is represented by mathematical expression (3), and $\vec{x}$ that is a predicted value acquired by multiplying the square matrix M by the square matrix F is represented by mathematical expression (4). In such a case, the data consistency evaluation function 216 derives a difference between element values in the first row as 0.2, derives a difference between element values in the second row as 0, derives a difference between element values in the third row as 0.2 and derives a difference between element values in the fourth row as 0 by comparing the mathematical expression (1) with mathematical expression (4).

[Expression 2]

$$\vec{y} = \begin{bmatrix} 0.1 \\ 0 \\ 0.4 \\ 0 \end{bmatrix} \quad (2)$$

[Expression 3]

$$\vec{x} = \begin{bmatrix} 0.3 \\ 0.2 \\ 0.6 \\ 0.1 \end{bmatrix} \quad (3)$$

[Expression 4]

$$MF\vec{x} = \begin{bmatrix} 0.3 \\ 0 \\ 0.6 \\ 0 \end{bmatrix} \quad (4)$$

For example, on the assumption that each DNN included in the medical image reconstruction model 300 can predict k-space data Dk with an ideal accuracy of 100%, when the square matrices M and F are multiplied by $\vec{x}$, $\vec{x}$ is consistent with $\vec{y}$ and a difference between $\vec{x}$ and $\vec{y}$ is not generated. That is, collected k-space data Dk is consistent with predicted k-space data Dk. However, practically, it is not easy to cause a DNN to predict k-space data Dk with perfect accuracy, and thus $\vec{x}$ and $\vec{y}$ always differ from each other by a not-so-little amount, $\vec{x}$ and $\vec{y}$ to be not consistent with each other.

Accordingly, the data consistency evaluation function 216 updates the predicted value $\vec{x}$ to the actually measured value $\vec{y}$ in order to eliminate a difference generated between $\vec{x}$ and $\vec{y}$, in other words, in order to cause $\vec{x}$ and $\vec{y}$ to be consistent with each other, for example. In the case of numerical examples of the aforementioned mathematical expressions (2) to (4), the data consistency evaluation function 216 updates an element value 0.3 of the first row of $\vec{x}$ to 0.1 which is the element value of the first row of $\vec{y}$ and updates an element value 0.6 of the third row of $\vec{x}$ to 0.4 which is the element value of the third row of $\vec{y}$. Meanwhile, when $\vec{x}$ and $\vec{y}$ are represented by transposed vectors, the aforementioned N-th row may be replaced with N-th column. N is an arbitrary natural number.

The data consistency evaluation function 216 may update element values of $\vec{x}$ to a statistical index value such as the average of the element values of $\vec{x}$ and element values of $\vec{y}$ instead of updating the element values of $\vec{x}$ to the element values of $\vec{y}$ in order to cause $\vec{x}$ and $\vec{y}$ to be consistent with each other. Accordingly, a matrix having $\vec{x}$ updated based on $\vec{y}$ as element values is input to a following DNN.

Furthermore, the data consistency evaluation function 216 may exchange the element values of $\vec{x}$ with a solution of a problem which minimizes mathematical expression (5) with respect to $\vec{x}$ (or an approximate solution thereof). This method can also be applied in the case of non-Cartesian data.

[Expression. 5]

$$\|MF\vec{x} - \vec{y}\|_2^2 + \lambda \|\vec{x} - \vec{x}_0\|_2^2 \quad (5)$$

In mathematical expression (5), $\vec{x}_0$ denotes $\vec{x}$ before being updated and $\vec{x}$ denotes $\vec{x}$ after being updated, $\vec{y}$ denotes a vector representing each element of collected k-space data Dk, and λ denotes arbitrary constant equal to or greater than 0.

Meanwhile, although an example in which the number of elements is 4 has been described in the aforementioned mathematical expressions (2) to (4) in order to simplify description, the present embodiment is not limited thereto and the number of elements may be timely changed according to a matrix representing k-space data Dk like 256×256 elements.

The reconstructed image evaluation function 218 evaluates a reconstructed image output from each encoder included in the medical image reconstruction model 300.

For example, when a reconstructed image is output from the first encoder 310 at the foremost stage among a plurality of encoders included in the medical image reconstruction model 300, the reconstructed image evaluation function 218 derives a statistical noise amount from the reconstructed image and determines whether the derived noise amount is less than a certain threshold value. For example, the threshold value with respect to the noise amount is set to a value of a degree to which a reconstructed image is regarded as an image having sufficient picture quality. The reconstructed image evaluation function 218 evaluates (determines) the reconstructed image as an image having sufficient picture quality when it is determined that the noise amount is less than the threshold value. On the other hand, the reconstructed image evaluation function 218 evaluates (determines) the reconstructed image as an image that does not have sufficient picture quality when it is determined that the noise amount is equal to or greater than the threshold value. The noise amount is an example of "index value representing quality."

When the reconstructed image evaluation function 218 evaluates the reconstructed image output from the first encoder 310 as an image having sufficient picture quality, the aforementioned reconstruction processing function 214 does not input the reconstructed image to the first decoder 312 and does not cause the second DNN 316 at the subsequent stage to generate a reconstructed image.

On the other hand, when the reconstructed image evaluation function 218 evaluates the reconstructed image output from the first encoder 310 as an image that does not have sufficient picture quality, the reconstruction processing function 214 inputs the reconstructed image to the first decoder 312 and causes the second DNN 316 at the subsequent stage to generate a reconstructed image.

In response to this, the reconstructed image evaluation function 218 waits until the second encoder 318 at the second stage outputs a reconstructed image, and when the second encoder 318 outputs a reconstructed image, derives a statistical noise amount from the reconstructed image and determines whether the derived noise amount is less than the threshold value. The reconstruction processing function 214 causes a DNN at a further subsequent stage to generate a reconstructed image when the reconstructed image evaluation function 218 evaluates the reconstructed image output from the second encoder 318 as an image that does not have sufficient picture quality. In this manner, the reconstruction processing function 214 causes the medical image reconstruction model 300 to continuously generate reconstructed images until the reconstructed image evaluation function 218 evaluates a reconstructed image as an image having sufficient picture quality.

When the reconstructed image evaluation function 218 evaluates a reconstructed image output from each encoder following the second encoder 318, the reconstructed image evaluation function 218 may determine whether a difference (a difference or mean square between absolute values, or the like) between a reconstructed image of a previous stage and a reconstructed image of the corresponding stage is less than the threshold value, evaluates the reconstructed image of the corresponding stage as an image having sufficient picture quality when it is determined that the difference from the reconstructed image of the previous stage is less than the threshold value, and evaluates the reconstructed image of the corresponding stage as an image that does not have sufficient picture quality when it is determined that the difference from the reconstructed image of the previous stage is equal to or greater than the threshold value instead of or in addition to evaluation based on a noise amount. A difference between a reconstructed image of a previous stage and a reconstructed image of a current stage is another example of "index value representing quality."

Further, the reconstructed image evaluation function 218 may evaluate picture quality of a reconstructed image according to whether the reconstructed image includes noise having a certain characteristic. For example, when an object in an elliptical shape is present at the center of a medical image generated by the medical image photographing apparatus 100, it is known that objects in a semicircular shape easily appear as a noise at upper and lower portions of a reconstructed image. When a noise that may appear according to the shape or position of such an object present in the original image has been detected from a reconstructed image, the reconstructed image evaluation function 218 may evaluate the reconstructed image as an image that does not have sufficient picture quality. A numerical value (for example, 1 or 0) indicating the presence or absence of noise that may appear depending on the shape or position of an object present in the original image is another example of "index value representing quality."

Although description has been made in such a manner that the reconstruction processing function 214 determines whether to cause the second DNN 316 at the subsequent stage to generate a reconstructed image based on results of evaluation of picture quality of a reconstructed image performed by the reconstructed image evaluation function 218, the present embodiment is not limited thereto. For example, the reconstruction processing function 214 may determine whether to cause the second DNN 316 at the subsequent stage to generate a reconstructed image based on results of evaluation of consistency of k-space data Dk performed by the data consistency evaluation function 216. For example, when the data consistency evaluation function 216 has evaluated $\vec{x}$ representing predicted k-space data Dk and $\vec{y}$ representing collected k-space data 11k as being inconsistent with each other due to a difference generated between $\vec{x}$ and $\vec{y}$, the reconstruction processing function 214 inputs a reconstructed image to the first decoder 312 and causes the second DNN 316 at the subsequent stage to generate a reconstructed image. Further, when the data consistency evaluation function 216 has evaluated $\vec{x}$ and $\vec{y}$ as being consistent with each other, the reconstruction processing function 214 does not input a reconstructed image to the first decoder 312 and does not cause the second DNN 316 at the subsequent stage to generate a reconstructed image. In this case, the difference between $\vec{x}$ and $\vec{y}$ is another example of "index value expressing quality".

The output control function 220 outputs a reconstructed image evaluated as an image having sufficient picture quality by the reconstructed image evaluation function 218 to the medical image photographing apparatus 100, a terminal device, and the like connected through the communication interface 202, for example. In addition, the output control function 220 may cause the display 206 to output (display) a reconstructed image.

For example, when a reconstructed image output from the first encoder 310 of the first stage has been evaluated as an image having sufficient picture quality, that is, it has been determined that the second DNN 316 of the subsequent stage is not caused to generate a reconstructed image, the output control function 220 outputs the reconstructed image output from the first encoder 310. Further, when a reconstructed image output from the first encoder 310 of the first stage has been evaluated as an image that does not have sufficient picture quality and thus it has been determined that the second DNN 316 of the subsequent stage is caused to generate a reconstructed image, if a reconstructed image output from the second encoder 318 at a further subsequent stage is evaluated as an image having sufficient picture quality, the output control function 220 outputs the reconstructed image output from the second encoder 318. In this manner, the output control function 220 outputs a reconstructed image at a point in time when picture quality is evaluated as sufficient. Further, when a reconstructed image having sufficient picture quality is not output from each encoder until the number of times of processing of generating a reconstructed image reaches a predetermined upper limit number of times, the output control function 220 may output, for example, a finally output reconstructed image without depending on picture quality evaluation results. The output control function 220 may output characters or an image for notifying a diagnostic reader that the picture quality of the reconstructed image is not sufficient along with the reconstructed image.

The output control function 220 may output a reconstructed image based on k-space data Dk (i.e., $\vec{x}$) evaluated as being consistent with $\vec{y}$ by the data consistency evaluation function 216 instead of or in addition to outputting a reconstructed image evaluated as an image having sufficient picture quality by the reconstructed image evaluation function 218.

[Processing Flow]

Figure 8:
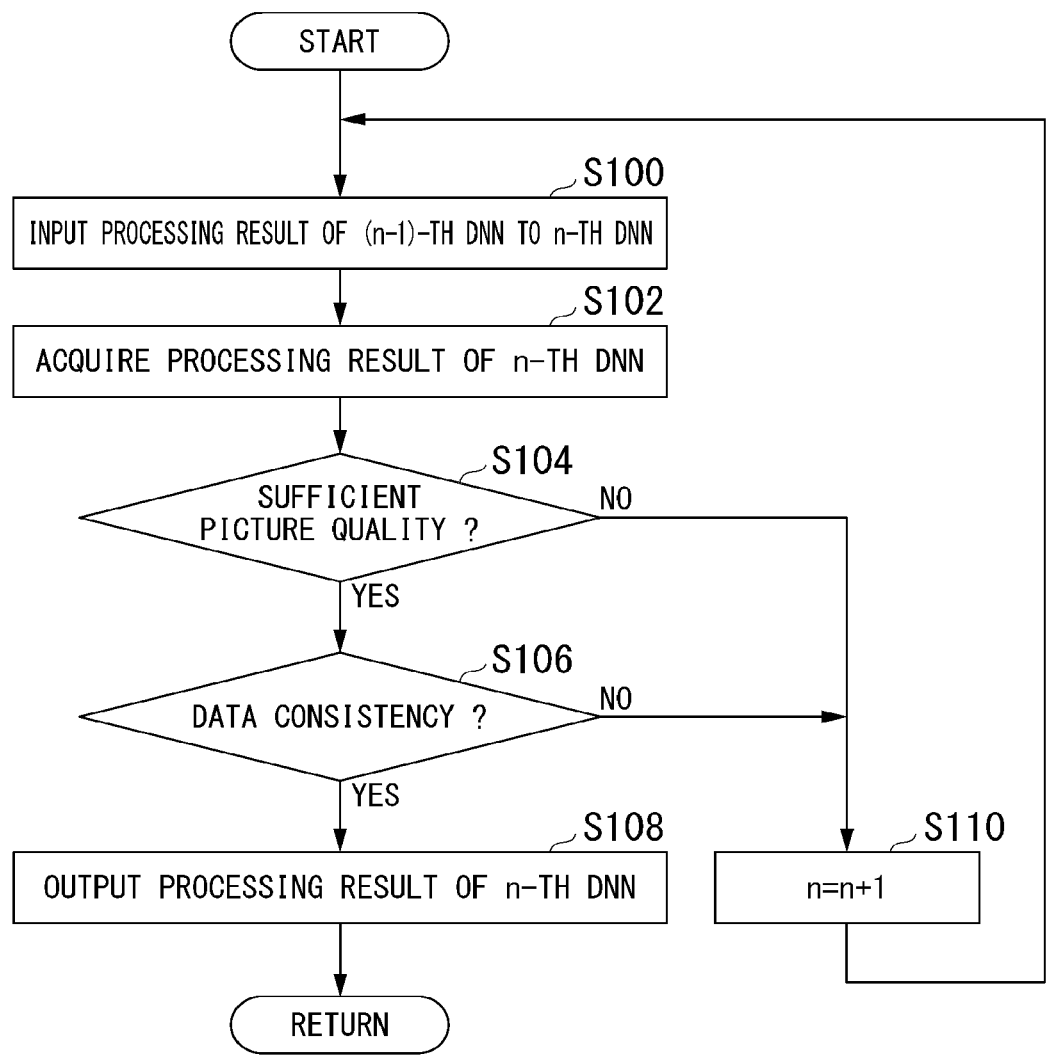
FIG. 8 is a flowchart showing the flow of a series of processes of a processing circuit in the present embodiment.

Hereinafter, a flow of a series of processes of the processing circuit 210 in the present embodiment will be described based on a flowchart. FIG. 8 is a flowchart showing a flow of a series of processes of the processing circuit 210 in the present embodiment. The processes of this flowchart may start when k-space data Dk has been acquired through the acquisition function 212, for example, and may be repeated at a predetermined period until the number of reconstructed image generation processes reaches a predetermined upper limit number of times.

First, the reconstruction processing function 214 inputs a processing result of an (n−1)-th DNN to an n-th DNN of the medical image reconstruction model 300 represented by the medical image reconstruction model information 232 (step S100). "n" represents a temporary parameter indicating one DNN of interest among a plurality of DNNs included in the medical image reconstruction model 300. For example, when n is 1, the reconstruction processing function 214 inputs k-space data Dk processed in the conversion layer 302 and the activation layer 304 to the first DNN 308 at the first stage. Accordingly, a reconstruction image is generated by the first DNN 308 at the first stage.

Next, the reconstructed image evaluation function 218 acquires a reconstructed image which is a processing result of the n-th DNN (step S102) and determines whether the acquired reconstructed image has sufficient picture quality (step S104).

When the reconstructed image evaluation function 218 has determined that the reconstructed image has sufficient picture quality, the data consistency evaluation function 216 compares k-space data Dk (i.e., $\vec{x}$) which is information before converting into the reconstructed image determined to have sufficient picture quality with k-space data Di (i.e., $\vec{y}$) input to the DNN in the process of S100 to determine whether $\vec{x}$ and $\vec{y}$ are consistent with each other (step S106). Meanwhile, the order of the process of S104 and the process of S106 may be reversed.

The output control function 220 outputs the reconstructed image that is the processing result of the n-th DNN which has been acquired in the process of S102 when the reconstructed image evaluation function 218 has determined that the reconstructed image has sufficient picture quality and the data consistency evaluation function 216 has determined that $\vec{x}$ and $\vec{y}$ which have become the source of the reconstructed image are consistent with each other, for example (step S108). Further, the output control function 220 may output the reconstructed image in any of a case where the reconstructed image evaluation function 218 has determined that the reconstructed image has sufficient picture quality and a case where the data consistency evaluation function 216 has determined that $\vec{x}$ and $\vec{y}$ which have become the source of the reconstructed image are consistent with each other, as described above.

On the other hand, the reconstruction processing function 214 increments the temporary parameter n when the reconstructed image evaluation function 218 has determined that the reconstructed image does not have sufficient picture quality or the data consistency evaluation function 216 has determined that $\vec{x}$ and $\vec{y}$ which have become the source of the reconstructed image are not consistent with each other, for example (step S110). Then, the reconstruction processing function 214 returns to the process of S100. Accordingly, when n is set to 1 and the first DNN 308 of the first stage is a DNN of interest, for example, the reconstruction processing function 214 changes the second DNN 316 of the second stage to a DNN of interest. As a result, the reconstruction processing function 214 inputs a processing result of the first decoder 312 to the second DNN 316 of the second stage. Accordingly, the processes of this flowchart end.

[Method of Learning Medical Image Reconstruction Model]

Hereinafter, a method of learning the medical image reconstruction model 300 will be described. For example, the reconstruction processing function 214 inputs k-space data Dk which has not been interleaved to the foremost DNN of the medical image reconstruction model 300, that is, the first DNN 308, acquires a reconstructed image generated by the first DNN 308 as teacher data in advance. Then, the reconstruction processing function 214 inputs interleaved k-space data Dk to the first DNN 308 and causes parameters (e.g., coefficients of a kernel function, and the like) of the first DNN 308, the conversion layer 302, the activation layer 304, the first modulation layer 306, the first encoder 310, and the like to be learned such that a reconstructed image generated by the first DNN 308 becomes close to the reconstructed image which is the teacher data acquired in advance. For example, the reconstruction processing function 214 may cause the parameters to be learned using gradient methods such as Stochastic Gradient Descent (SGD), momentum SGD, AdaGrad, RMSprop, AdaDelta, and Adaptive moment estimation (Adam).

The reconstruction processing function 214 inputs, to the n-th DNN following the second stage, a reconstructed image generated by the (n−1)-th DNN when k-space data Dk that has not been interleaved is input, and acquires a reconstructed image generated by the n-th DNN as teacher data in advance. It is assumed that the (n−1)-th DNN has been sufficiently learned. Then, the reconstruction processing function 214 inputs, to the n-th DNN, a reconstructed image generated by the (n−1)-th DNN when interleaved k-space data Dk is input, and causes parameters of the n-th DNN, an n-th modulation layer, an (n−1)-th decoder, an n-th encoder, and the like to be learned such that a reconstructed image generated by the n-th DNN becomes close to the reconstructed image which is the teacher data.

When n is 2, for example, the reconstruction processing function 214 inputs a result (matrix) acquired by the first decoder 312 processing a reconstructed image generated by the first DNN 308 when k-space data Dk that has not been interleaved is input to the second DNN 316 and acquires a reconstructed image generated by the second DNN 316 as teacher data. Next, the reconstruction processing function 214 inputs a result (matrix) acquired by the first decoder 312 processing a reconstructed image generated by the first DNN 308 when interleaved k-space data Dk is input to the second DNN 316 and causes parameters of the second DNN 316, the second modulation layer 314, the first decoder 312, the second encoder 318, and the like to be learned such that a reconstructed image generated by the second DNN 316 becomes close to the reconstructed image which is the teacher data.

In this manner, DNNs are sequentially caused to learn from a previous stage to a subsequent stage among a plurality of DNNs connected in series by repeating a process of sufficiently learning the first DNN 308, learning the second DNN 316 based on a processing result of the sufficiently learned first DNN 308 and learning a following DNN. Consequently, it is possible to generate a reconstructed image with high picture quality even when an image reconstruction process has been ceased halfway because parameters are learned for each DNN. Meanwhile, it may be possible to cause parameters of all DNNs connected in series to be straightly learned such that a reconstructed image that is an output result of the DNN of the final stage becomes close to a reconstructed image (teacher data) acquired from k-space data Dk that has not been interleaved through a Fourier transform, instead of causing DNNs to sequentially learn from preceding DNNs.

According to the above-described first embodiment, it is possible to generate a medical image with high accuracy (high picture quality) while reducing a processing time by including the acquisition function 212 which acquires k-space data Dk (an example of first data), and the reconstruction processing function 214 which causes the first DNN 308 and the first encoder 310 to output a reconstructed image (an example of second data) based on the k-space data Dk acquired by the acquisition function 212, causes the second DNN 316 and the second encoder 318 to output a reconstructed image (an example of third data) based on a result (matrix) acquired by the first decoder 312 processing the reconstructed image output by the first DNN 308 and the first encoder 310, and determines whether to cause the second DNN 316 of the subsequent stage to generate a reconstructed image based on picture quality of the reconstructed image caused to be output by the first encoder 310.

In general, there are cases in which a processing time is prioritized over picture quality because the time for which a patient is restricted on the bed 104 of the medical image photographing apparatus 100 in order to capture medical images such as MR images and CT images is limited. Particularly, in the case of a patient who requires emergency medical care, it is necessary to rapidly generate medical images. In the present embodiment, it is possible to generate medical images with high picture quality by dynamically changing the quantity of processing operations necessary to reconstruct the medical images in accordance with the situation of a medical service spot because the processing circuit 210 determines whether to cause a DNN of a subsequent stage to generate a reconstructed image based on results of evaluation of picture quality of reconstructed images.

(Modified Example of First Embodiment)

Hereinafter, a modified example of the first embodiment will be described. Although data input to the medical image reconstruction model 300 is k-space data Dk in the above-described first embodiment, the present embodiment is not limited thereto. For example, data input to the medical image reconstruction model 300 may be data corresponding to each element of k-space data Dk, hybrid spatial data acquired by Fourier transforming k-space data Dk, or a medical image itself. In this case, the hybrid spatial data and the medical image are other examples of the "first data." When k-space data Dk alone is input to the medical image reconstruction model 300, the conversion layer 302 may be a full connected layer rather than a convolution layer.

Although the medical image reconstruction model 300 includes a plurality of DNNs configured in multiple stages in the above-described first embodiment, the present embodiment is not limited thereto. For example, the medical image reconstruction model 300 may be composed of a single RNN instead of a plurality of DNNs connected through multiple stages.

Figure 9:
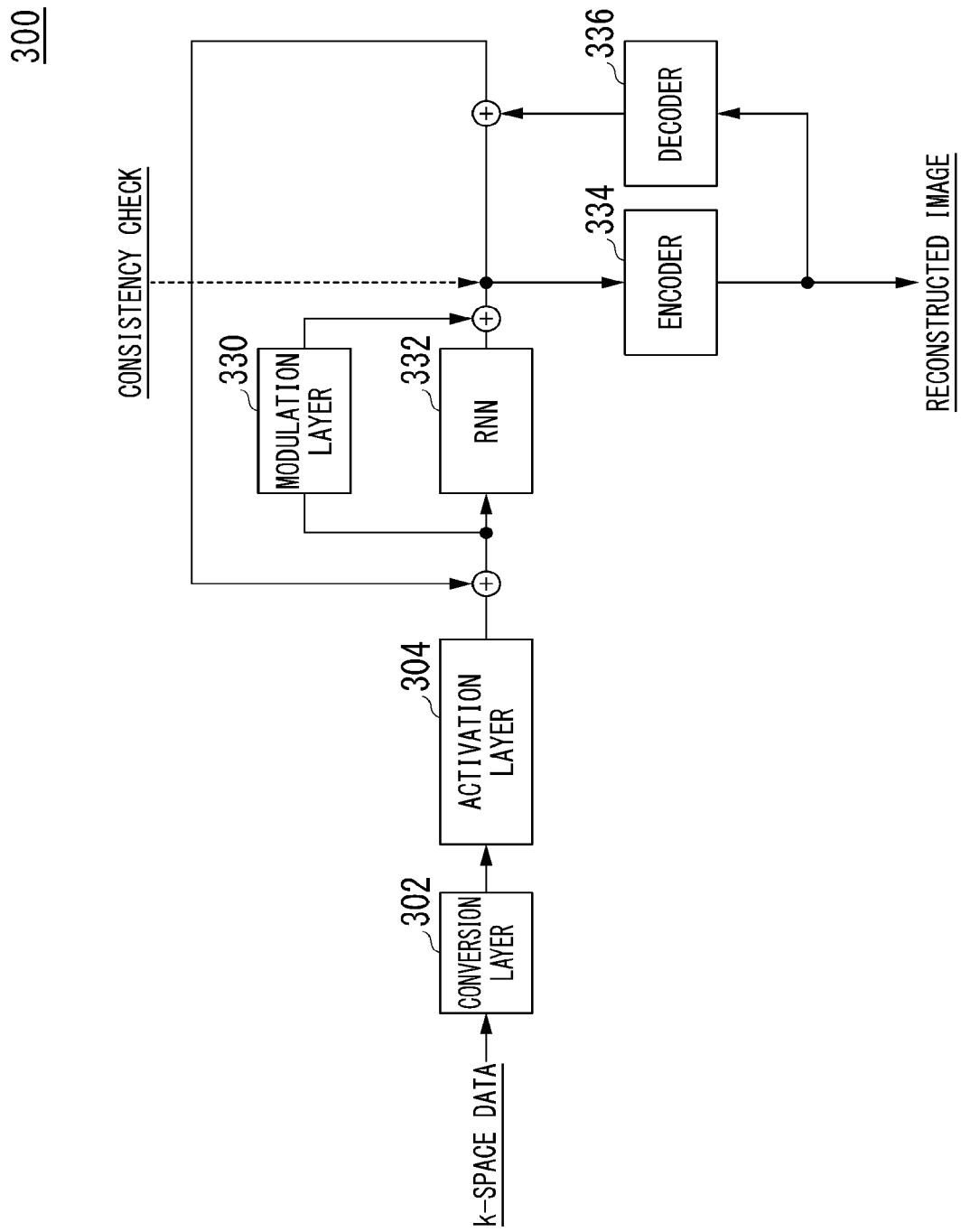
FIG. 9 is a diagram showing another example of the medical image reconstruction model.

FIG. 9 is a diagram showing another example of the medical image reconstruction model 300. As shown, the medical image reconstruction model 300 may include a conversion layer 302, an activation layer 304, a modulation layer 330, an RNN 332, an encoder 334, and a decoder 336, for example.

Like the above-described first modulation layer 306 and second modulation layer 314, the modulation layer 330 may be implemented as a layer of multiplying a weight, a layer of performing scaling, or the like.

The RNN 332 is a neural network which repeats a process at a predetermined period. For example, the RNN 332 generates a matrix representing k-space data Dk which becomes the source of a reconstructed image based on a processing result acquired in a previous period and data input in a current period.

The encoder 334 may be implemented as a convolution layer, for example, like the above-described first encoder 310 and second encoder 318. For example, the encoder 334 generates a matrix having the same numbers of rows and columns as those of a matrix of k-space data Dk based on output data from the modulation layer 330 and output data from the RNN 332. The second encoder 318 generates a reconstructed image which has been reconstructed using k-space data Dk by performing an inverse Fourier transform on a generated matrix and outputs the reconstructed image. On the other hand, the encoder 334 may output the generated matrix as it is without performing an inverse Fourier transform or while performing an inverse Fourier transform.

The decoder 336 may be implemented as a convolution layer, for example, like the above-described first decoder 312 and second decoder 320. When a reconstructed image has been output from the encoder 334, the decoder 336 generates a matrix representing k-space data Dk from the reconstructed image by performing a Fourier transform on the reconstructed image, for example. In addition, the decoder 336 may not perform a Fourier transform when the encoder 334 has output a matrix representing k-space data Dk instead of a reconstructed image. A processing result output by the decoder 336 is treated as input data in the next processing period of the RNN 332. Accordingly, it is possible to generate medical images with high accuracy (high picture quality) while reducing a processing time as in the first embodiment.

Furthermore, although the medical image photographing apparatus 100 and the medical information processing apparatus 200 are different apparatuses in the above-described first embodiment, the present embodiment is not limited thereto. For example, the medical information processing apparatus 200 may be implemented as a function of the console device 120 of the medical image photographing apparatus 100. That is, the medical information processing apparatus 200 may be a virtual machine virtually implemented as the console device 120 of the medical image photographing apparatus 100.

Figure 10:
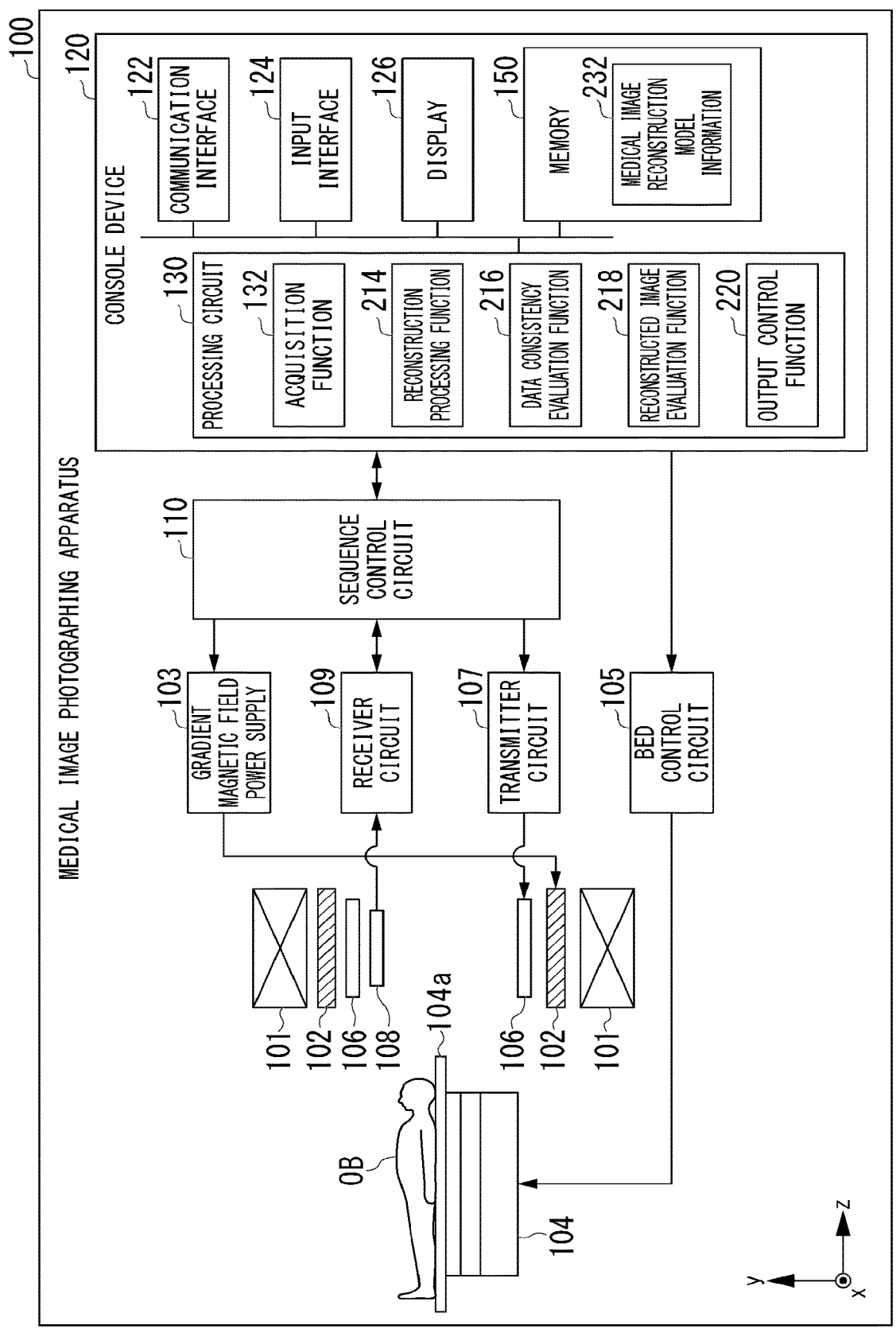
FIG. 10 is a diagram showing another example of the medical image photographing apparatus according to the first embodiment.

FIG. 10 is a diagram showing another example of the medical image photographing apparatus 100 according to the first embodiment. As shown in FIG. 10, the processing circuit 130 of the console device 120 may execute the reconstruction processing function 214, the data consistency evaluation function 216, the reconstructed image evaluation function 218 and the output control function 220 in addition to the aforementioned acquisition function 132.

The memory 150 of the console device 120 may store the medical image reconstruction model information 232.

According to such a configuration, it is possible to generate medical images with high accuracy (high picture quality) while reducing a processing time through the medical image photographing apparatus 100 alone.

Second Embodiment

Hereinafter, a second embodiment will be described. The second embodiment differs from the first embodiment in that conditions in which a DNN of a subsequent stage is caused to generate a reconstructed image are changed based on a photographing schedule of the medical image photographing apparatus 100. Hereinafter, description will be made focusing on a difference from the first embodiment and description of common points in the first and second embodiments will be omitted. Further, the same reference signs are attached to the same parts as those in the first embodiment in the description of the second embodiment.

The data consistency evaluation function 216 of the processing circuit 210 in the second embodiment changes evaluation conditions when data consistency is evaluated according to a photographing schedule, for example. A photographing schedule is information in which an execution time for medical image reconstruction has been determined in response to an examination type (presence or absence of contrast medium administration, or the like) and a portion to be photographed. The execution time for medical image reconstruction represents a waiting time which indicates how long a patient should wait during an image photographing interval.

In general, in an examination of administrating a contrast medium and photographing a test object, it is necessary to generate a reconstructed image within a shorter time compared to an examination of photographing a test object without administrating a contrast medium. In such a case, it is desirable to reduce a time required to evaluate data consistency. Accordingly, the data consistency evaluation function 216 do not evaluate data consistency or may evaluate data consistency with severity when photographing for which contrast medium administration has been determined is performed to prioritize reduction of a processing time over picture quality of a reconstructed image.

There are cases in which patients should hold their breaths in order to improve the picture quality of medical images when parts such as an abdomen and a chest are photographed in an MRI apparatus and a CT apparatus. In this case, there is a relatively long interval until the next photographing in order to allow patients to relax after photographing ends. Accordingly, the data consistency evaluation function 216 may loosely evaluate data consistency to prioritize improvement of picture quality over a processing time required to reconstruct an image when parts such as an abdomen and a chest are photographed.

FIG. 11 is a diagram showing an example of a photographing schedule. As in the shown example, when a long execution time for image reconstruction has been secured for photographing without contrast medium administration and a short execution time for image reconstruction has been secured for photographing with contrast medium administration in the photographing schedule, the data consistency evaluation function 216 may set loose evaluation conditions for photographing without contrast medium administration and set tight evaluation conditions for photographing with contrast medium administration. More specifically, the data consistency evaluation function 216 may reduce an allowable range regarded as generating a difference between $\vec{x}$ and $\vec{y}$ for photographing without contrast medium administration and increase the allowable range regarded as generating a difference between $\vec{x}$ and $\vec{y}$ for photographing with contrast medium administration.

Further, the reconstruction processing function 214 of the processing circuit 210 in the second embodiment may change an upper limit number of times of the medical image reconstruction model 300 being caused to output a reconstructed image in accordance with a photographing schedule. For example, the reconstruction processing function 214 may increase the upper limit number of times for photographing without contrast medium administration and decrease the upper limit number of times for photographing with contrast medium administration.

When conditions pertaining to generation of a reconstructed image are changed in this manner, it is difficult for the processing circuit 210 to cause a DNN of a subsequent stage to generate a reconstructed image when photographing with contrast medium administration is performed, compared to photographing without contrast medium administration, because it is necessary to reduce waiting times of patients. Accordingly, it is possible to provide a reconstructed image to a diagnostic reader more rapidly.

Meanwhile, the aforementioned photographing schedule is merely an example. In the case of a schedule in which the next photographing will be performed after circulation of a contrast medium through a test part from contrast medium administration, for example, the processing circuit 210 may decrease the allowable range or increase the upper limit number of times in order to improve the picture quality of a reconstructed image of an image captured before contrast medium administration because there is a time until the next photographing. Accordingly, a processing operation time required to reconstruct a medical image is permitted to increase and thus a DNN of a subsequent stage can be easily caused to generate a reconstructed image. Consequently, it is possible to provide a reconstructed image with higher accuracy to a diagnostic reader.

Moreover, the aforementioned evaluation conditions and upper limit number of times of image reconstruction may be timely changed by doctors, diagnostic readers, and the like. For example, the output control function 220 causes the display 206 or a screen of a terminal device connected through the communication interface 202 to display a screen for changing the evaluation conditions and upper limit number of times of image reconstruction as a GUI. Accordingly, when the evaluation conditions and upper limit number of times of image reconstruction have been changed through the GUI, the processing circuit 210 acquires an electrical signal representing an operation of changing the evaluation conditions and upper limit number of times of image reconstruction, which has been received by the display 206 or the terminal device, from that device and changes the evaluation conditions and upper limit number of times of image reconstruction based on the acquired electrical signal.

According to the above-described second embodiment, it is possible to reduce a text time and mitigate the burden of patients because images are reconstructed according to a predetermined photographing schedule. In examination such as MRI, patients are made remain in hospitals until it is visually confirmed that all MR images have been normally captured, and if it is confirmed that some MR images have not been normally captured, retest is performed on the spot in preparation for cases in which MR images have not been captured with high accuracy, in general. Accordingly, if a long time is required for reconstruction, patients need to wait for a long time and thus the burdens of the patients easily increase. On the other hand, in the second embodiment, it is possible to end a reconstruction process before the next photographing timing and provide a reconstructed image to a diagnostic reader and the diagnostic reader can check whether a medical image has been normally acquired for each photographing because a time required to reconstruct a medical image is dynamically changed according to an examination type (presence or absence of contrast medium administration, and the like) and a part to be photographed. As a result, the number of works for re-performing one or more previous photographing operations because the next photographing is started before a reconstructed medical image is checked can be reduced, and thus the burdens of patients can be decreased.

Further, according to the above-described second embodiment, it is possible to provide reconstructed images to diagnostic readers such as doctors in real time because images are reconstructed according to predetermined photographing schedules, and thus diagnostic readers can give diagnoses in real time while viewing medical images and appropriately determine a next body part to be photographed.

Third Embodiment

Hereinafter, the third embodiment will be described. The third embodiment differs from the first embodiment and the second embodiment described above in that the threshold value for the image quality of the reconstructed image is changed based on the processing time allowed for the medical image reconstruction model 300. In the following explanation, the differences from the first embodiment and the second embodiment will be mainly described, and the description in common with the first embodiment or the second embodiment will be omitted. In the description of the third embodiment, the same elements as those of the first embodiment and the second embodiment will be denoted with the same reference numerals.

In the third embodiment, the reconstruction processing function 214 allows each DNN included in the medical image reconstruction model 300 to reconstruct the medical image within a certain period, and in a case where the DNN cannot reconstruct the medical image within the acceptable time, the reconstruction processing function 214 outputs the processing result of the DNN of the previous stage.

The reconstruction processing function 214 determines an acceptable processing time (hereinafter referred to as acceptable time) for the DNN based on the external environment of the medical information processing apparatus 200. For example, when the medical information processing apparatus 200 receives a request for reconstructing a medical image from the medical image photography apparatus 100, the medical information processing apparatus 200 stores the request in the memory 230 in a data structure such as a queue. The medical image photographing apparatus 100 reconstructs the medical image in response to each request stored in the memory 230.

At this time, the reconstruction processing function 214 changes the acceptable time for the DNN according to the number of requests stored in the memory 230. For example, the reconstruction processing function 214 shortens the acceptable time as the number of requests increases, and increases the acceptable time as the number of requests decreases.

The reconstruction processing function 214 may change the acceptable time for the DNN according to the number of medical image photographing apparatuses 100 connected to the medical information processing apparatus 200 via the network NW, that is, the number of modalities. For example, the reconstruction processing function 214 shortens the acceptable time as the number of modalities increases, and increases the acceptable time as the number of modalities decreases.

At this time, the reconstruction processing function 214 may weight an acceptable time for the DNN in accordance with the type of the medical image photographing apparatus 100 which is the modality. For example, where the processing load required to reconstruct an MR image in response to a request by an MRI apparatus is 1 and the processing load required to reconstruct a CT image in response to a request by a CT apparatus is 2, the reconstruction processing function 214 may increase the acceptable time for DNN when performing reconstruction processing in response to a request from the MRI apparatus than when performing reconstruction processing in response to a request from the CT apparatus.

When the reconstruction processing function 214 determines an acceptable time for the DNN, the reconstruction processing function 214 changes a threshold value for an index value indicating the image quality of the reconstructed image in accordance with the acceptable time. For example, the reconstruction processing function 214 increases the threshold value for noise amount as the acceptable time for DNN decreases. As a result, the noise amount acquired from the reconstructed image tends to be less than the threshold value, and the reconstructed image evaluation function 218 is likely to evaluate (determine) that the reconstructed image has a sufficient image quality. As a result, the reconstruction processing function 214 does not input the reconstructed image that has been evaluated to have sufficient image quality to a decoder of a subsequent stage, making it difficult for the DNN of the subsequent stage to generate the reconstructed image.

The reconstruction processing function 214 may change, as a threshold value for the index value indicating the image quality of the reconstructed image, a threshold value for the difference between a reconstructed image of the DNN of the previous stage and a reconstructed image of the DNN of the current stage and a threshold value for the difference between $\vec{x}$ and $\vec{y}$, instead of or in addition to changing the threshold value for the noise amount.

The reconstruction processing function 214 may change a threshold value for the index value indicating the image quality of the reconstructed image based on the processing time actually taken by each DNN. For example, in a case where the time it takes for the first encoder 310 to output the reconstructed image since the k-space data Dk is input to the conversion layer 302 is less than the threshold value, then the reconstruction processing function 214 inputs the reconstructed image output from the first encoder 310 into the first decoder 312 to cause the second DNN 316 of the subsequent stage to reconstruct the image. On the other hand, in a case where the time it takes for the first encoder 310 to output the reconstructed image since the k-space data Dk is input to the conversion layer 302 is equal to or more than the threshold value, then the reconstruction processing function 214 does not input the reconstructed image output from the first encoder 310 into the first decoder 312. In response to this, the output control function 220 transmits the reconstructed image output by the first encoder 310 to the medical image photographing apparatus 100 via the communication interface 202 or causes the display 206 to display the reconstructed image.

According to the third embodiment described above, a threshold value for an index value such as noise amount or difference of images is changed according to the acceptable time for DNN and the processing time actually required for DNN, so that increasing the responsiveness to requests can be prioritized over improving the image quality of reconstructed images.

Other Embodiments

Hereinafter, other embodiments will be described. In the above-described embodiments, the medical information processing apparatus 200 has been described as outputting the reconstructed image output by the medical image reconstruction model 300 to an external apparatus such as the medical image photography apparatus 100, but the above-described embodiments are not limited thereto. For example, the medical information processing apparatus 200 may output data that has not yet been encoded into a reconstructed image, i.e., data (matrix) to be input into the encoder, to an external apparatus that can encode the image.

In a case where the reconstructed image output by the DNN of the current stage is not sufficient in image quality, the medical information processing apparatus 200 may output the reconstructed image output by the DNN of the previous stage, and may also output the reconstructed image output by the DNN of the current stage in addition to the reconstructed image output by the DNN of the previous stage. In a case where the reconstructed image output by the DNN of the current stage is not sufficient in image quality, the medical information processing apparatus 200 may not output at least the reconstructed image output by DNN of the current stage (may output, however, the reconstructed image output by DNN of the previous stage), and instead, may output information indicating that the reconstructed image is not sufficient in image quality.

The medical information processing apparatus 200 compares the image quality of the reconstructed image output by the DNN of the current stage with the image quality of the reconstructed image output by the DNN of the previous stage, and in a case where the image quality of the reconstructed image of the current stage is degraded compared to the image quality of the reconstructed image of the previous stage, the medical information processing apparatus 200 may print the reconstructed image of the previous stage instead of outputting the reconstructed image of the current stage.

In the above-described embodiments, the medical image reconstruction model 300 is a model including two or more DNNs, but the embodiment is not limited thereto. As described above, DNN is a combination of a plurality of linear functions and a plurality of non-linear functions (activation functions). For example, the medical image reconstruction model 300 may not be a neural network acquired by combining a plurality of linear functions and a plurality of nonlinear functions, but may be a network acquired by combining only a plurality of nonlinear functions including learnable parameters. Such networks are, for example, Kervolutional Neural Networks (see, C. Wang et al. Kervolutional Neural Networks. arXiv: 1904.03955. 2019.)

According to at least one of the above-described embodiments, it is possible to generate medical images with high accuracy (high picture quality) while reducing a processing time by including the acquisition function 212 which acquires k-space data Dk, and the reconstruction processing function 214 which causes the first DNN 308 and the first encoder 310 to output a reconstructed image based on the k-space data Dk acquired by the acquisition function 212, causes the second DNN 316 and the second encoder 318 to output a reconstructed image based on a result (matrix) acquired by the first decoder 312 processing the reconstructed image output by the first DNN 308 and the first encoder 310, and determines whether to cause the second DNN 316 of the subsequent stage to generate a reconstructed image based on picture quality of the reconstructed image caused to be output by the first encoder 310.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
    a processor configured to
        acquire first data collected for medical imaging of a test object, wherein the first data is k-space data corresponding to a space in which the test object is present;
        input the acquired first data into a first model including a first neural network, and output second data from the first model receiving the first data, wherein the second data is a first reconstructed magnetic resonance (MR) image;
        determine, based on picture quality of the second data, whether the second data is to be input into a second model which includes a second neural network;
        when determining that the second data is to be input into the second model, input the second data into the second model, and output third data which is output from the second model receiving the second data, wherein the third data is a second reconstructed magnetic resonance image different from the first reconstructed MR image;
        when determining that the second data is not to be input into the second model, output at least the second data without inputting the second data into the second model,
    wherein the processor is further configured to
        derive a noise amount of the second data,
        determine whether the derived noise amount is equal to or more than a threshold value,
        when determining that the derived noise amount is equal to or more than the threshold value, input the second data into the second model, and
        when determining that the derived noise amount is less than the threshold value, not input the second data into the second model.

2. The medical information processing apparatus according to claim 1, wherein the processor is further configured to determine whether the second data is to be input into the second model based on a predetermined processing time for the first model.

3. The medical information processing apparatus according to claim 2, wherein when an index value representing a quality of the second data is equal to or more than a threshold value, the processor is further configured to input the second data into the second model,
    when the index value is less than the threshold value, the processor is further configured to not input the second data into the second model, and
    the processor is further configured to increase the threshold value as the predetermined processing time is shorter.

4. The medical information processing apparatus according to claim 3, wherein the processor is further configured to determine the predetermined processing time based on an external environment.

5. The medical information processing apparatus according to claim 1, wherein the processor is further configured to determine whether the second data is to be input into the second model based on a processing load required for processing using the first model.

6. The medical information processing apparatus according to claim 1, wherein when the first data and the second data are not consistent, the processor is further configured to input the second data into the second model, and when the first data and the second data are consistent, the processor is further configured to not input the second data into the second model.

7. The medical information processing apparatus according to claim 1, wherein the first model generates the second data from the first data in first processing, and
the second model generates the third data from the second data in second processing, the second processing being of a same type as the first processing.

8. The medical information processing apparatus according to claim 1, wherein the first model is a model that has learned to output the second data when the first model receives the first data, and
the second model is a model that has learned to output the third data when the second model receives the second data.

9. The medical information processing apparatus according to claim 8, wherein the first model and the second model are neural networks based on a composite function acquired by combining one or more linear functions and one or more non-linear functions.

10. The medical information processing apparatus according to claim 8, wherein the first model and the second model are neural networks based on a composite function acquired by combining one or more non-linear functions.

11. The medical information processing apparatus according to claim 1, wherein when the first data and the second data are not consistent, the processor is further configured to update the second data with fourth data based on the first data, and input the fourth data into the second model.

12. A medical information processing apparatus, comprising:
a first processing circuit including a first neural network; and
a second processing circuit including a second neural network, wherein the second processing circuit is configured to generate third data from second data received from the first processing circuit, wherein the first processing circuit is configured to:
acquire first data collected for medical imaging of a test object, wherein the first data is k-space data corresponding to a space in which the test object is present;
generate the second data from the acquired first data, wherein the second data is a first reconstructed magnetic resonance (MR) image;
determine, based on picture quality of the second data, whether the generated second data is to be input into the second processing circuit; and
when determining that the second data is to be input into the second processing circuit, input the second data into the second processing circuit, the second processing circuit being then configured to generate and output the third data, wherein the third data is a second reconstructed magnetic resonance image different from the first reconstructed MR image;
when determining that the second data is not to be input into the second processing circuit, output at least the second data without inputting the second data into the second processing circuit,
wherein the first processing circuit is further configured to
derive a noise amount of the second data,
determine whether the derived noise amount is equal to or more than a threshold value,
when determining that the derived noise amount is equal to or more than the threshold value, input the second data into the second model, and
when determining that the derived noise amount is less than the threshold value, not input the second data into the second model.

13. A medical information processing method for causing a processor to execute a method comprising:
acquiring first data collected for medical imaging of a test object, wherein the first data is k-space data corresponding to a space in which the test object is present;
inputting the acquired first data into a first model including a first neural network, and outputting second data from the first model receiving the first data, wherein the second data is a first reconstructed magnetic resonance (MR) image;
determining, based on picture quality of the second data, whether the second data is to be input into a second model which includes a second neural network;
when determining that the second data is to be input into the second model, inputting the second data into the second model, and outputting at least third data from the second model receiving the second data, wherein the third data is a second reconstructed magnetic resonance image different from the first reconstructed MR image;
when determining that the second data is not to be input into the second model, outputting at least the second data without inputting the second data into the second model, wherein the method further includes
deriving a noise amount of the second data;
determining whether the derived noise amount is equal to or more than a threshold value;
when determining that the derived noise amount is equal to or more than the threshold value, determining to input the second data into the second model; and
when determining that the derived noise amount is less than the threshold value, determining not to input the second data into the second model.

14. A medical information processing apparatus, comprising:
a processor configured to
acquire first data collected for medical imaging of a test object;
input the acquired first data into a first model including a first neural network, and output second data from the first model receiving the first data;
determine, based on picture quality of the second data, whether the second data is to be input into a second model which includes a second neural network;
when determining that the second data is to be input into the second model, input the second data into the second model, and output third data, which is output from the second model receiving the second data;
when determining that the second data is not to be input into the second model, output at least the second data without inputting the second data into the second model, wherein the processor is further configured to
derive a noise amount of the second data,
determine whether the derived noise amount is equal to or more than a threshold value,
when determining that the derived noise amount is equal to or more than the threshold value, input the second data into the second model, and
when determining that the derived noise amount is less than the threshold value, not input the second data into the second model,
wherein the first data is a first reconstructed magnetic resonance (MR) image, the second data is a second reconstructed magnetic resonance image different from the first reconstructed MR image, and the third data is a third reconstructed magnetic resonance image different from the second reconstructed MR image.

15. A medical information processing apparatus, comprising:
- a first processing circuit including a first neural network; and
- a second processing circuit including a second neural network, wherein the second processing circuit is configured to generate third data from second data received from the first processing circuit, wherein the first processing circuit is further configured to
- acquire first data collected for medical imaging of a test object;
- generate the second data from the acquired first data;
- determine, based on picture quality of the second data, whether the generated second data is to be input into the second processing circuit; and
- when the first processing circuit determines that the second data is to be input into the second processing circuit, input the second data into the second processing circuit, the second processing circuit being then configured to generate and output the third data;
- when the first processing circuit determines that the second data is not to be input into the second processing circuit, the first processing circuit outputs at least the second data without inputting the second data into the second processing circuit, wherein the first processing circuit derives a noise amount of the second data, wherein the first processing circuit determines whether the derived noise amount is equal to or more than a threshold value, wherein, when the derived noise amount is equal to or more than the threshold value, the first processing circuit determines to input the second data into the second model, and wherein, when the derived noise amount is less than the threshold value, the first processing circuit determines not to input the second data into the second model, wherein the first data is a first reconstructed magnetic resonance (MR) image, the second data is a second reconstructed magnetic resonance image different from the first reconstructed MR image, and the third data is a third reconstructed magnetic resonance image different from the second reconstructed MR image.

16. A medical information processing method for causing a processor to execute a method comprising:
- acquiring first data collected for medical imaging of a test object;
- inputting the acquired first data into a first model including a first neural network, and outputting second data from the first model receiving the first data;
- determining, based on picture quality of the second data, whether the second data is to be input into a second model which includes a second neural network;
- when the processor determines that the second data is to be input into the second model, inputting the second data into the second model, and outputting at least third data from the second model receiving the second data;
- when the processing circuitry determines that the second data is not to be input into the second model, outputting at least the second data without inputting the second data into the second model,
- deriving a noise amount of the second data;
- determining whether the derived noise amount is equal to or more than a threshold value;
- when the derived noise amount is equal to or more than the threshold value, determining to input the second data into the second model; and
- when the derived noise amount is less than the threshold value, determining not to input the second data into the second model, wherein the first data is a first reconstructed magnetic resonance (MR) image, the second data is a second reconstructed magnetic resonance image different from the first reconstructed MR image, and the third data is a third reconstructed magnetic resonance image different from the second reconstructed MR image.

* * * * *